US012806273B2

(12) United States Patent
Fransen et al.

(10) Patent No.: US 12,806,273 B2
(45) Date of Patent: Nov. 24, 2026

(54) HYDROGEL COMPOSITION FOR THE TREATMENT OF PERITONEAL DISEASES

(71) Applicant: UPyTher B.V., Eindhoven (NL)

(72) Inventors: Peter Paul Kathleen Hubert Fransen, Eindhoven (NL); Gerardus Cornelis Van Almen, Son en Breugel (NL); Patricia Yvonne Wilhelmina Dankers, Helmond (NL)

(73) Assignee: UPyTher B.V., Eindhoven (NL)

( * ) Notice: Subject to any disclaimer, the term of this patent is extended or adjusted under 35 U.S.C. 154(b) by 0 days.

(21) Appl. No.: 19/300,569

(22) Filed: Aug. 14, 2025

(65) Prior Publication Data

US 2026/0034222 A1 Feb. 5, 2026

Related U.S. Application Data

(63) Continuation of application No. PCT/NL2024/050072, filed on Feb. 14, 2024.

(30) Foreign Application Priority Data

Feb. 15, 2023 (NL) ...................................... 2034155

(51) Int. Cl.

| | |
|---|---|
| ***A61K 47/34*** | (2017.01) |
| ***A61K 9/00*** | (2006.01) |
| ***A61K 9/06*** | (2006.01) |
| ***A61K 31/337*** | (2006.01) |
| ***A61K 31/407*** | (2006.01) |
| ***A61K 31/4745*** | (2006.01) |
| ***A61K 31/497*** | (2006.01) |

(52) U.S. Cl.

CPC ............ *A61K 47/34* (2013.01); *A61K 9/0019* (2013.01); *A61K 9/06* (2013.01); *A61K 31/337* (2013.01); *A61K 31/407* (2013.01); *A61K 31/4745* (2013.01); *A61K 31/497* (2013.01)

(58) Field of Classification Search

None

See application file for complete search history.

(56) References Cited

FOREIGN PATENT DOCUMENTS

WO WO-2014185779 A1 * 11/2014 ........... C08G 18/664
WO WO 2019/016208 A1 1/2019

OTHER PUBLICATIONS

Dankers, P.Y.W., et al., Convenient formulation and application of a supramolecular ureido-pyrimidinone modified poly(ethylene glycol) carrier for intrarenal growth factor delivery, European Polymer Journal 72 (2015) 484-493 (Year: 2015).*
International Search Report and Written Opinion received in PCT Application No. PCT/NL2024/050072 as mailed May 17, 2024 in 8 pages.
Bakker et al., "Cholesterol Modification of an Anticancer Drug for Efficient Incorporation into aSupramolecular Hydrogel System," Macromolecular Rapid Communications, vol. 39, Issue 17, May 28, 2018.
Bakker et al., "Supporting Information—Cholesterol Modification of an Anticancer Drug for Efficient Incorporation into a Supramolecular Hydrogel System," Macromolecular Rapid Communications, vol. 39, No. 17, May 28, 2018 in 7pages.
Kieltyka et al., "Mesoscale Modulation of Supramolecular Ureidopyrimidinone-Based Poly(ethylene glycol) Transient Networks in Water," Journal of the American Chemical Society, vol. 135, Issue 30, pp. 11159-11164.

* cited by examiner

*Primary Examiner* — H. Sarah Park
(74) *Attorney, Agent, or Firm* — Knobbe, Martens, Olson & Bear, LLP

(57) ABSTRACT

The present disclosure relates to a hydrogel composition for use in the treatment or prevention of a peritoneal disease, wherein the hydrogel composition may include a UPy-PEG polymer and a pharmaceutically acceptable carrier. The hydrogel composition may include a pharmaceutically active agent. The hydrogel composition may be used to treat peritoneal carcinomatosis or peritoneal metastasis.

20 Claims, 15 Drawing Sheets

6 wt%

7 wt%

8 wt%

R848

MEDI9197

HYDROGEL COMPOSITION FOR THE TREATMENT OF PERITONEAL DISEASES

TECHNICAL FIELD

The present invention relates to a hydrogel composition for the treatment or prevention of a peritoneal disease.

BACKGROUND

Peritoneal Cavity

The peritoneum lines the peritoneal cavity and is the largest and most complex serous membrane of the human body. It is a three dimensional organ covering the intra-abdominal (visceral peritoneum) organs and the abdominal wall (parietal peritoneum) including the interior surface of the diaphragm. It consists of a monolayer of mesothelial cells supported by a basement membrane and multiple layers of connective tissue with a total thickness of 90 μm.

The visceral peritoneum, also covering the mesentery, forms a continuous layer with the parietal peritoneum, which lines the abdominal wall and pelvic cavities. It can be seen as a large sac that tethers and covers the abdominal organs but still enables considerable mobility. The peritoneal membrane has a surface area of 1.5-2 $m^2$, similar to the skin, but is much larger if all microvilli are taken into account which is important for the role of the peritoneum as a transport barrier in intraperitoneal chemotherapy.

The peritoneal cavity is the largest serosal sac and fluid-filled cavity and contains 150-200 ml of fluid. Just like other serous membranes such as the pleura, the peritoneum secretes serous fluid (nearly 50 ml per day). The function of the peritoneum and the peritoneal fluid is to reduce friction between intraabdominal organs and the abdominal wall. It is important in the host's defense against intraabdominal infection as it is a barrier to infectious agents and is ripe with innate and adaptive immune cells.

The peritoneal cavity is an established route for the administration of drugs, such as painkillers after laparoscopy and for peritoneal dialysis. Intraperitoneal instillation of anticancer drugs is used to treat peritoneal abdominal cancers. Several structures, including the peritoneal fluid, mesothelium, intervening interstitium and blood vessel wall together compose a complex diffusion barrier: the peritoneal-plasma barrier. This means that after intraperitoneal administrations, drugs have to cross various different structures to get to the blood circulation. Vice versa, this barrier also inhibits obtaining effective intraperitoneal concentrations with systemic chemotherapy that is administered to the bloodstream.

The peritoneal cavity is a common injection site but its use as a common route of administration is hindered by several obstacles:

- The peritoneal cavity has a very irregular and complex topology with some areas that are difficult to access, especially after the formation of adhesions.
- The peristaltic motion of the gastrointestinal organs or mobility of the body cause internal movement.
- It is the largest fluid-filled cavity in the human body and requires large volumes for effective distribution which can be painful and harmful.

Peritoneal Carcinomatosis

Peritoneal carcinomatosis comprises a heterogenous group of different cancers with various degrees of peritoneal spreading. Peritoneal carcinomatosis can be primary tumours of the peritoneum (peritoneal mesothelioma and primary peritoneal cancer) or peritoneal metastasis from tumors of other sites, including intraperitoneal origins (gastrointestinal, gynecological (e.g. ovarian) and sarcoma) and also extraperitoneal sites (lung, skin, kidney).

In general, peritoneal carcinomatosis is under-diagnosed as the detection with routine imaging techniques is difficult, due to their small size and the limited contrast resolution of soft tissues. Therefore the real incidence of peritoneal carcinomatosis is unclear. For colorectal cancer it is estimated that 10-40% present with peritoneal metastases during disease but at autopsy this number can be as high as 80%. For gastric cancer, 1 in 2 patients have peritoneal carcinomatosis and ovarian cancer is notorious as 80% develops peritoneal spreading. The development of peritoneal carcinomatosis is often associated with rapid disease progression and poor prognosis as it will produce bowel obstruction, the formation of malignant ascites, visceral pain, and malnutrition.

The development of peritoneal carcinomatosis can be seen as a stepwise process starting with cancer cells penetrating the peritoneal cavity from the primary tumor site. Then cells can detach from the primary tumor and adhere to the peritoneal mesothelium and then further invade the submesothelial tissue. Common sites for the formation of peritoneal tumor spots are dispersed: the omentum, mesentery, bowel surface, pouch of Douglas, right paracolic gutter, and diaphragm. For this reason, a homogenous distribution of intraperitoneal chemotherapy is required to reach all disease sites.

Peritoneal carcinomatosis is not effectively treatable by systemic chemotherapy, and as a result the occurrence of the disease is considered a terminal disease. However, in many cases the metastatic spreading is confined to the peritoneal cavity: 10-35% for colorectal cancer, and 50% for gastric cancer. For ovarian cancer, the peritoneal cavity is mostly the only site of metastasis during the course of disease. All these patients ultimately die from local complications due to the tumor burden, without systemic metastasis. For patients with liver and/or extraperitoneal metastases, the overall survival is still determined by the occurrence of peritoneal carcinomatosis. Metastasis to the peritoneum is therefore the bottleneck in the treatment of gastrointestinal and ovarian cancers.

Surgical treatment with curative intent is only available to a small group of patients with favorable disease status. A semiquantitative measure of the peritoneal tumor load, the peritoneal cancer index (PCI) is used to assess the disease burden and is an important tool for selecting patients who are eligible for cytoreductive surgery. Usually only less than 10% is deemed operable, leaving a large group of inoperable patients without an effective treatment. In view of the treatment options, patients can be stratified by their disease burden:

- Patients with advanced peritoneal carcinomatosis (PCI>20) who are considered inoperable because of their disease burden
- Patients with low-moderate stage peritoneal carcinomatosis (PCI<20) who are eligible for surgery and intraperitoneal chemotherapy
- Patients who don't have peritoneal disease yet, but are at risk of developing it later after resection of a primary tumor.

Drugs for Intraperitoneal Chemotherapy

No drug formulations are specifically designed for intraperitoneal administration. Current intraperitoneal chemotherapy relies on the off-label use of products developed for intravenous administration. These formulations are rapidly cleared from the peritoneal cavity through the capillaries and lymphatic systems, and cause local and systemic toxicity after systemic absorption.

Different parameters have to be considered to develop the optimal drug product for intraperitoneal therapy:

AUC ratio between peritoneal cavity and plasma—Drug exposure in the peritoneal cavity and plasma can be described by the area under the curve (AUC), which is the integral of concentration over time. The cavity-to-plasma AUC ratio determines how much of the drug is retained in the peritoneal cavity and how much is systemically absorbed. A large cavity-to-plasma ratio is important to have high drug exposure in the peritoneal cavity with few systemic toxic effects, the so-called pharmacokinetic advantage of intraperitoneal chemotherapy.

Tumor penetration depth—The limited tumor penetration of chemotherapeutic drugs is one of most important problems in intraperitoneal chemotherapy. The penetration depth of drugs that are intraperitoneally delivered is estimated to be maximally 2 to 5 mm. The stroma of the tumor tissue is difficult to penetrate and extended exposure time is required to overcome this barrier.

Cell cycle phase specificity—Current intraperitoneal chemotherapy relies mostly on the use of drugs that are non-cell cycle phase specific which already work at short exposure time. However, the effect of both cell cycle phase specific and non-specific drugs is enhanced with longer exposure times.

Systemic toxicity—Systemic toxicity is usually minimal after intraperitoneal administration of chemotherapeutics because only a small amount of drug is present in the systemic compartment at a certain time. The amount of drug in the systemic compartment depends on the pharmacokinetic profile of the drug and the dose. At high doses toxicity can be hematological or renal, and therefore high dose are not recommended.

Intrinsic activity of the agent against the primary tumor type.

A formulation that can achieve a continuous prolonged drug release would result in a significant improvement in all parameters described above. Despite the peritoneal-plasma barrier, small molecule drugs are still rapidly cleared from the peritoneal cavity through the peritoneal capillaries into the systemic circulation. Mitomycin C has a half-life of 60-90 minutes in the peritoneal cavity, whereas other drugs such as paclitaxel and docetaxel are cleared in less than day. The short dwell time in the peritoneal cavity inhibits the therapeutic effectiveness of the drug and necessitates frequent or continuous dosing. To overcome this bottle-neck, new formulations need to be developed specifically for the peritoneal cavity to control the drug release and avoid a systemic peak exposure.

It is not recommended to use higher dose to improve the therapeutic effectiveness. The pharmacokinetics of mitomycin C, for example, are linear. This means that an increase in the intraperitoneal concentrations produces a proportional increase in the plasma exposure. With current dosing regimens of 35 mg/m2, 28% of the patients developed severe bone marrow suppression still, which would become unacceptable at higher doses.

For multiple drugs it is known that their efficacy is not only dose-dependent, but also exposure time dependent. Francescutti et al. demonstrated that mice with peritoneal metastases that were given an intraperitoneal chemotherapy lavage of mitomycin C for 90 minutes had a better survival than with a lavage of 60 minutes. Ozawa et al. showed that the cell killing action of mitomycin is dependent on the product of concentration and time using in vitro studies with tumor cell lines. If the exposure time is shorter than one hour, a high concentration of 5 μg/ml mitomycin C is needed to kill 90% of the cells in culture. If the exposure time is extended to more than 10 hours, a low concentration of only 0.1 μg/ml is required to kill 90% of the cells. The cytotoxic effect of mitomycin C, a cell cycle phase-non-specific drug, is caused by the irreversible alkylating reaction of mitomycin with DNA. Because of the irreversibility of the reaction, the damage caused to the DNA accumulates as the drug exposure time is prolonged.

Colin et al. demonstrated using an in silico model that a lower dose and longer exposure time will improve treatment efficacy with minimal systemic toxicity. Higher concentrations of paclitaxel in the peritoneal fluid will result in a saturation point where the amount of drug in the tumor ($AUC_{tumor}$) will not increase further. Only by extending the exposure time the amount of drug in the tumor can increase. The maximum $AUC_{tumor}$ is 4.30, 13.09, 26.24 and 35.00 μg·h/g for the 15, 45, 90 and 120 min treatments and therefore linearly increases with exposure time. Paclitaxel, like docetaxel and 5-FU, is a cell cycle phase specific drug which requires a longer period of cell contact to get cell death because the cell needs to in a specific phase of the mitotic cycle to have an effect.

Thus for both types of chemotherapeutic drugs is it clear that maintaining the drug exposure for a longer time will result in a more effective treatment.

The Rationale for Intraperitoneal Drug Delivery

The pharmacokinetic advantage of intraperitoneal chemotherapy is the most important rational for the locoregional treatment of peritoneal carcinomatosis. The peritoneal-plasma barrier limits the absorption of drug from the peritoneal cavity into the blood. This absorption is much slower than the clearance of drug from the systemic compartment (i.e. by metabolism or excretion). As a result the pharmacokinetic advantage is a high local concentration with a longer residence time of the drug in the peritoneal cavity, improving drug exposure to the cancer cells, combined with lower systemic exposure and toxicity.

The goal of the approaches to improve intraperitoneal drug delivery is to obtain higher drug concentration at the site of disease combined with less toxicity to healthy tissues. However, despite the clear pharmacokinetic advantage of intraperitoneal chemotherapy, tumor tissue penetration depth is still limited and high intraperitoneal fluid drug concentrations may not correlate with increased drug amounts in tumors. Moreover, in spite of the plasma-peritoneum barrier, drug compounds are still rapidly cleared from the peritoneal cavity through the capillaries and lymphatic systems, and cause local and systemic toxicity after systemic absorption due to the high doses that are used.

Drug penetration is dependent on diffusion to maintain a concentration gradient. After intraperitoneal administration, drugs enter the tumors by passive diffusion. However, the tumor environment is characterized by a high interstitial pressure that counters the rapid diffusion of drugs. Tumors with a volume larger than a few millimeters will not be adequately exposed due to the limited tissue penetration of intraperitoneal chemotherapy. For example, a single 30 minutes chemotherapy perfusion is inadequate to efficiently kill the entire tumor cell population, and even more so when using cell cycle specific chemotherapy. In order to overcome this effect, exposure needs to be prolonged to build a concentration gradient that allows the drug molecules time to passively diffuse into the tumors.

New formulations are needed to fulfill the potential of intraperitoneal drug delivery. Therapeutic compounds should be retained more effectively in the peritoneal cavity to enhance the pharmacokinetic advantage (i.e. better AUC ratio) and improve drug penetration, therapeutic action, and local and systemic toxicity. The formulation should have the necessary properties to overcome challenges of the peritoneal cavity with regards to shape, mobility, size and volume and effectively retain and release drug compounds in an aqueous environment. It should be easy to introduce the formulation to the peritoneal cavity using common, simple clinical procedures. After performing its function, the formulation should be resorbed from the peritoneal cavity and eliminated from the body without causing adverse reactions.

Current Clinical Techniques for Intraperitoneal Drug Delivery

CRS+HIPEC

The most common treatment for peritoneal carcinomatosis is cytoreductive surgery (CRS) combined with hyperthermic intraoperative intraperitoneal chemotherapy (HIPEC). All visible tumor spots are manually removed by the surgeon and afterwards the abdomen is flushed for 30-90 minutes with a large volume of highly concentrated heated chemotherapy solution to kill all remaining tumor cells. The surgery can be performed optimally by an experienced surgeon. However, the limited time of treatment, and drug exposure is a severe disadvantage resulting in tumor regrowth and recurrence (Ceelen). Another drawback of HIPEC is the necessity to perform the technique in the operating room after surgery, requiring specialized equipment and trained personnel. HIPEC can only be performed in combination with surgery, therefore only a small group of patients is eligible to undergo HIPEC due to the heavy burden of the total procedure.

EPIC

In early intraperitoneal chemotherapy (EPIC), treatment follows surgery for 4-6 days postoperatively, adding a few extra days of treatment. Here, the drug is infused through an intraperitoneal catheter which was placed before closing the abdomen after completing surgery. The chemotherapy treatment is usually started on the first postoperative day. The use of EPIC is hampered by the higher risk of complications after CRS, due to the prolonged exposure of the healthy and damaged operated tissues to the high dose of chemotherapy. The large volume also causes less comfort for the patient due to abdominal distention. Moreover, with EPIC it is difficult to achieve an even distribution of the chemotherapy in the abdomen. The peritoneal cavity is inhomogeneous and surgical adhesions restrict access to all areas. As a result, instillation by catheter often fails to reach all peritoneal surfaces at risk.

PIPAC

During pressurized intraperitoneal aerosol chemotherapy (PIPAC), a capnoperitoneum (peritoneal cavity filled with CO2 gas at a pressure of 12 mm Hg) is established to apply chemotherapy in the form of an aerosol. It is thought that the aerosol distributes better throughout the peritoneal cavity and that the high pressure improves tissue penetration. However, also here adhesions as a result of surgery create obstacles that limit aerosol diffusion. And importantly, drug exposure is limited to a short period of time thereby failing to produce sufficient cell-killing activity.

Drug Delivery Technologies Used for Intraperitoneal Drug Delivery

Intraperitoneal therapies fail mainly because of poor drug delivery to the tumor. No chemotherapeutic formulations are designed or approved for intraperitoneal use. Current local intraperitoneal strategies use products that are developed for systemic administration but are rapidly cleared from the peritoneal cavity, and cause systemic toxicity due to high blood concentrations following systemic uptake. Multiple drug delivery technologies have been explored to extend the residence time of the drug in the peritoneal cavity and improve intraperitoneal therapy.

Microspheres—Depending on their size, microspheres can have a longer retention time in the peritoneal cavity. Microspheres smaller than 8 μm are cleared from the peritoneal cavity through the lymphatic system. Microspheres are also associated with inflammatory reactions and peritoneal adhesions, thereby raising serious safety concerns.

Liposomes—Liposomes are widely used as drug carriers for hydrophilic (inside the liposome core) and hydrophobic (in the lipid bilayer) compounds. But liposomes are rapidly cleared from the peritoneal cavity due to their small size (<1000 nm).

Nanoparticles—Also nanoparticles are unable to remain in the peritoneal cavity for extended periods of time but are effective in penetrating the tumors.

Micelles—Micellular formulations of hydrophobic drugs, such as paclitaxel or docetaxel, are already used in intraperitoneal chemotherapy. However the surfactant that is used in the formulations is not well tolerated and causes hypersensitivity reactions of peritoneal tissues.

Hydrogels for Intraperitoneal Drug Delivery

Hydrogels are considered as the most promising system for the local intraperitoneal treatment of peritoneal carcinomatosis. Hydrogels are three-dimensional cross-linked networks, either by physical or covalent cross-links, with a semi-solid morphology. The three-dimensional network can absorb a large volume of water, similar to biological tissue, and can hold active therapeutic ingredients. Hydrogels can encapsulate therapeutic compounds and release them locally in a continuous and prolonged manner. The release is governed by various mechanisms such as diffusion, hydrogel degradation, electrostatic interactions, swelling and external stimuli such as changes in pH, ionic strength, and temperature.

Hydrogels can function as a physical barrier to prevent adhesions. But most importantly, they can serve as a macroscopic depot that retains the drug in the peritoneal cavity. The major technical difficulty hampering the use of hydrogels is the control over the viscosity to enable minimally invasive administration and uniform distribution of a stable depot in the peritoneal cavity. Materials with a low viscosity that behave as a liquid can distribute freely but are unable to retain drug compounds whereas highly viscous materials are difficult to handle and administer.

Thermosensitive polymers are very important biomaterials used as drug delivery vehicles. Their sol-gel transition can be tuned through the design of the polymer to enable liquid-like behavior at room temperature, and transition to a semi-solid gel at physiological temperature. The key to the behavior of thermosensitive materials is the balance between hydrophilic and hydrophobic segments of the polymers. At temperatures below the lower critical solution temperature (LCST), the polymer is soluble. Upon increasing the temperature above the LCST, the polymer changes to an insoluble state, for example a micellar aggregate.

Thermosensitive hydrogels are considered promising drug delivery systems because the temperature-sensitive properties enables injectability for local administration. However, these materials are brittle and prone to disintegrate after administration (Cho & Kwon). WO2011089604A2 discloses injectable thermoreversible hydrogels based on Pluronic polymers for the delivery of drugs to internal cavities, especially mitomycin C to the bladder. These materials dissolve rapidly in physiological fluids and may not provide the drug exposure for the required amount of time.

Supramolecular hydrogels based on UPy-PEG polymers comprise a different class of injectable materials and are already disclosed in the prior art (Bakker et al.; Bastings et al.) However, this class of telechelic polymers is not always suitable for intraperitoneal use as the formed hydrogels may fall apart into small fragments after administration due to undesired brittle properties.

The prior art teaches that many hydrogel systems have been tried in the peritoneal cavity but fail to address all the technical challenges. The optimal hydrogel formulation for application in intraperitoneal drug delivery should have a viscosity that enables easy administration and uniform distribution of the formulation into the peritoneal cavity with its irregular and complex topology. It should be possible to control the sol-gel transition of the material such that it adheres to and coats the entire peritoneum and possible disease sites. Once applied in the peritoneal cavity, the formulation should be soft and elastic to prevent mechanical damage to the soft tissues inside the abdominal cavity. The formulation needs to remain in place long enough to have a therapeutic effect and/or retain the active therapeutic ingredients to prolong drug exposure but should ultimately be resorbed and eliminated by the body's natural processes. No adverse health effects should occur. The formulation should also be suitable to carry different pharmaceutically active agents and provide effective release thereof.

The present invention now provides a hydrogel composition that fulfills the above requirements.

SUMMARY

The present invention relates to a hydrogel composition for use in the treatment or prevention of a peritoneal disease, wherein the hydrogel composition comprises:

a) UPy-PEG polymer and b) a pharmaceutically acceptable carrier, wherein the UPy-PEG polymer is obtainable by a process wherein a compound A with formula (I)

(I)

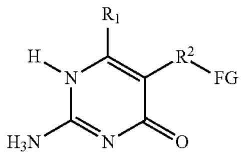

wherein $R^1$ is independently selected from the group consisting of hydrogen and $C_1$-$C_{20}$ alkyl, $R^2$ is $C_1$-$C_{20}$ alkyl, and FG is a functional group independently selected from OH and $N(R^1)H$ is reacted with a diisocyanate compound B with formula OCN—$R^3$—NCO wherein $R^3$ is $C_2$-$C_{16}$ alkyl or $C_4$-$C_{16}$ alkenyl and a polyethylene glycol C with formula OH—P—OH wherein P is a polymeric group having a $M_n$ of 250 to 50,000.

The present invention also provides a method of treatment or prevention of a peritoneal disease, comprising administering to a subject the hydrogel composition comprising the UPy-PEG polymer and the pharmaceutically acceptable carrier, as described above.

DETAILED DESCRIPTION

As described above, the present invention provides a hydrogel composition for use in the treatment or prevention of a peritoneal disease. The hydrogel composition of the invention has a viscosity profile that makes it possible to administer the hydrogel composition to the peritoneal cavity with conventional techniques. Once present in the peritoneal cavity, the viscosity of the hydrogel increases under the influence of the physiological parameters such as body temperature and pH.

The hydrogel composition of the invention is also shown to be able to provide a desired sustained release profile for different types of pharmaceutically active agents. The hydrogel composition is non-toxic and well absorbed by the body.

UPy-PEG Polymer

The UPy-PEG polymer used in the hydrogel composition can be prepared by the reaction of a compound A with formula (I), a diisocyanate compound B and a polyethylene glycol C as described above. Compounds A and B provide a hydrophobic segment and polyethylene glycol C provides a hydrophilic segment of the polymer.

In Formula (I) of compound A, $R^1$ is preferably $C_1$-$C_5$ alkyl, more preferably methyl. $R^2$ is preferably $C_1$-$C_5$ alkyl, more preferably ethyl. FG in compound A is preferably OH. Alkyl includes linear and branched alkyl, but is preferably linear alkyl.

In diisocyanate compound B, $R^3$ is preferably $C_4$-$C_{10}$ alkyl. The diisocyanate compound B is most preferably hexane diisocyanate (HDI).

HO—P—OH preferably represents a polyether, more preferably polyethylene glycol (PEG). The molecular weight $M_n$ of the PEG is preferably 250 to 50,000 Da. The Mn can be determined by end group titration. Preferably the $M_n$ is 5,000 to 30,000 Da, more preferably 15,000 to 25,000 Da. The polyethylene glycol is preferably telechelic with the reactive functional groups at chain ends.

The hydrophobic/hydrophilic behavior of the UPy-PEG polymer can be adjusted by adjusting the molar ratio's wherein compound A, diisocyanate compound B and polymer C molar are reacted. Preferably the molar ratio C:(A+B) is 1:1 to 1:15, preferably 1:2 to 1:11.

The UPy-PEG polymer used according to the invention can also be represented as $$[PEG—I—U—I—U—I]_n$$

wherein:

PEG is polyethylene glycol (polymer C)

I is an aliphatic diisocyanate (compound B)

U is a hydrogen bonding UPy-moiety (formula I)

I and U indicate the building blocks of the UPy-PEG polymer. During the reaction where the UPy-PEG polymer is formed the isocyanate is converted to a urea or urethane bond.

The UPy-PEG polymer preferably has a molecular weight Mn of 5,000 to 1,000,000 Da, more preferably 15,000 to 100,000 Da. The molecular weight can be determined by methods know to the skilled person, such as end group titration or size exclusion chromatography (SEC).

A class of such UPy-PEG polymers is known from WO2014/185779 which is incorporated herein by reference.

The UPy-PEG polymer can be prepared by reacting compounds A, B and C in an appropriate solvent in the presence of an appropriate catalyst by methods known in the art, for example in solution or in the bulk using reactive extrusion. The process is preferably performed at a temperature between about 10° C. and about 140° C., more preferably between about 20° C. and about 120° C., and most preferably between about 40° C. and about 90° C.

The process for the preparation of the UPy-PEG polymer may be performed in the presence of a catalyst. Examples of suitable catalysts are known in the art and they promote the reaction between isocyanates and hydroxyl groups. Preferred catalysts include tertiary amines and catalysts comprising a metal. Preferred tertiary amines are 1,4-diazabicyclo[2.2.2]octane (DABCO) and 1,8-diazabicyclo[5.4.0]undec-7-ene (DBU). Preferred catalysts comprising a metal are tin(IV) compounds and zirconium(IV) compounds, preferably selected from the group consisting of tin(II) octanoate, dibutyltin(IV)laurate and zirconium(IV)acetoacetate. Most preferably, the catalyst is dibutyltin(IV)laurate. The amount of catalyst is generally below about 1 wt. %, preferably below about 0.2 wt. % based on the total weight of reactants.

The process may be performed in the presence of a non-reactive organic solvent, wherein it is preferred that the amount of the non-reactive organic solvent is at least about 20 wt. %, more preferably at least about 40 wt. %, based on the total weight of the reaction mixture. It is also preferred that the reaction mixture does not comprise any inorganic solvents such as water.

Non-reactive solvents may be selected from non-protic polar organic solvents, preferably tetrahydrofuran, dioxane, N-methylpyrollidone, dimethylformamide, dimethylacetamide, dimethyl sulfoxide, propylene carbonate, ethylene carbonate and 2-methoxy-ethyl-acetate.

Viscosity Profile

The requirement for developing a hydrogel composition that can be administered to a body cavity is that the composition behaves as a liquid at near physiological conditions but responds to an external trigger (change in pH or temperature) to switch to a solid material. In particular, the formulation is liquid at room temperature (15 to 25° C.) outside the body and solid-like or gel-like inside the body cavity at pH 6 to 8 and temperature of 35 to 40° C.

Thus, the hydrogel composition has a viscosity of 1 to 2000 mPa·s, preferably 1 to 500 mPa·s over a temperature range of 15 to 25° C. and a pH range of 8 to 14. The composition at this temperature and pH is also referred to as the precursor solution. This solution shows sufficient flow properties and can be administered to the peritoneal cavity with methods known in the art.

Viscosity is determined at 20° C. by rotational rheology measurements using a conical plate geometry, with a fixed distance of 0.101 mm wherein shear viscosity is recorded as function of shear rate with 600 μL of liquid hydrogel solution applied onto the plate of the rheometer. The viscosity is measured at shear rate 1 $s^{-1}$.

Further the hydrogel composition has a viscosity of at least 100 mPa·s, preferably at least 1000 mPa·s over a temperature range of 35 to 40° C. and a pH range of 6 to 8. Upon administration of the precursor solution to the peritoneal cavity, the solution forms a hydrogel.

Preferably, the hydrogel composition shows Newtonian behavior, i.e. a constant viscosity at all shear rates, before administration (precursor) to the peritoneal cavity. After administration, the hydrogel shows non-Newtonian behavior.

Composition

The hydrogel composition of the invention comprises the UPy-PEG polymer and a pharmaceutically acceptable carrier, which is preferably an aqueous solution that may optionally contain a buffer. Preferably the pharmaceutically acceptable carrier is phosphate buffered saline (PBS) buffer solution. The carrier can also be used to adjust the pH of the hydrogel composition to obtain the viscosity profile as outlined above. Preferably the hydrogel composition has a pH of 8.0 to 14.

The concentration of the UPy-PEG polymer in the hydrogel composition is 0.5 to 20 wt. %, preferably 1 to 10 wt. %, more preferably 4 to 8 wt. %, based on the total weight of the hydrogel composition.

The hydrogel composition is prepared by dissolving the UPy-PEG polymer in the carrier. The carrier may be heated to a temperature of 30-80° C. to accelerate the dissolution. The pH of the composition can be adjusted by use of an appropriate buffer solution as the carrier. Alternatively, the pH can be adjusted after dissolving the UPy-PEG polymer, for instance by adding a sodium hydroxide or a hydrochloric acid solution.

According to a preferred embodiment, the hydrogel composition comprises:

4-9 wt. % UPy-PEG polymer obtained by reacting a compound A of formula (I) wherein $R^1$ is methyl, $R^2$ is ethylene and FG is OH, with hexanediisocyanate (B) and polyethylene glycol (C) with a molecular weight of 20 kDa 91-96 wt. % aqueous buffer, wherein the composition has a pH of 9.0-10.0 and wherein the wt. % is based on the total weight of the hydrogel composition.

The molar ratio of A:B:C is preferably 2:3:1.

Active Agents

The hydrogel composition of the invention allows for the incorporation of different pharmaceutically active agents that are known for the treatment or prevention of peritoneal diseases. The pharmaceutically active agent may be selected from antineoplastic drugs, chemotherapeutic agents, monoclonal antibodies, immunomodulating compounds, targeted therapies and combinations thereof.

According to an embodiment of the invention, the pharmaceutically active agent is selected from antineoplastic drugs and chemotherapeutic agents, in particular from mitomycin C, oxaliplatin, carboplatin, cisplatin, gemcitabine, 5-fluorouracil (5-FU), paclitaxel, docetaxel, irinotecan, doxorubicin and combinations thereof. According to another embodiment of the invention, the pharmaceutically active agent is selected from immunomodulating compounds such as TLR-agonists (imidazoquinolines), STING-agonists (cyclic dinucleotides) and combinations thereof. According to another embodiment of the invention, the pharmaceutically active agent is selected from targeted therapies such as ATR-inhibitors, PARP-inhibitors and combinations thereof. The hydrogel composition is also suitable for the combination of antineoplastic drugs and/or chemotherapeutic agents with targeted therapies.

One of the advantages of the invention is that the hydrogel composition may comprise both water soluble as well as less water soluble or water insoluble pharmaceutically active agents. The water insoluble active agents can be included in the hydrogel composition without the need of additives such as surfactants, DMSO or PEG400.

More hydrophobic active agents will have increased affinity with the hydrophobic compartments of the hydrogel and will be released at a slower rate than a more hydrophilic active agent. The hydrogel composition thus enables a synergetic sequential combination therapy.

Diseases

The hydrogel composition of the invention is used for the prevention or treatment of peritoneal diseases. With prevention is meant that the hydrogel composition can be administered before the disease occurs, for instance in the prevention of metastasis. With treatment is meant that the hydrogel composition decreases the disease or removes the disease all together. The treatment is administered to a mammal, in particular a human.

With peritoneal diseases is meant diseases that occur in the peritoneal cavity. According to a preferred embodiment, the peritoneal diseases comprise peritoneal carcinomatosis, including primary tumors of the peritoneum such as peritoneal mesothelioma and primary peritoneal cancer, and peritoneal metastasis from tumors of other sites, including intraperitoneal origins, such as gastrointestinal and ovarian cancer and sarcoma, and extraperitoneal origin sites such as lung, skin and kidney cancers. The present invention encompasses treatment of cancers, but also prevention of recurrence of cancers, i.e. metastasis. The invention is further suitable for the prevention of postsurgical peritoneal adhesions.

Method of Administration

According to an embodiment, the treatment of the diseases described above comprises administering the hydrogel composition to a peritoneal cavity. The hydrogel composition can be administered via a catheter, via injection or using nebulization such as pressurized intraperitoneal aerosol chemotherapy (PIPAC).

The invention also relates to a cartridge comprising the hydrogel composition of the invention. Such a cartridge can be used in existing methods and devices for administering a composition to the peritoneal cavity.

Sustained Release

As described above, one of the advantages of the invention is that the pharmaceutically active agent can be released in a controlled way. Thus the treatment of the invention comprises sustained release of the active agent. A preferred release rate is a rate of more than 80% in a time range of 2 to 30 hours for a hydrophilic active agent and of 2 to 30 days for a hydrophobic active agent.

This release rate can be determined by loading a model drug compound from a stock solution (30 mM in DMSO) to 0.3 mM in the hydrogel composition (precursor solution), transferring the drug loaded solution (100 μL) to a Millicell insert, placed in a 24-wells plate filled with PBS pH 7.4, 7.8 or 8.2 (600 μL), refreshing the PBS at set times and analyzing the removed PBS for drug content by UV absorbance, wherein the release experiments are performed with n=3. Other methods are LC-MS or ICP-MS. Such methods are known to a skilled person.

The present invention also provides a method of treating or preventing peritoneal malignancies comprising administering a hydrogel composition to a peritoneal cavity, wherein the hydrogel composition comprises the UPy-PEG polymer as described above, an effective amount of a pharmaceutically active agent and a pharmaceutically acceptable carrier.

According to an embodiment, the present invention comprises a method of treating peritoneal cancer and/or metastasis in a patient comprising intraperitoneally administering a hydrogel composition of the invention comprising an effective dose of a pharmaceutically active agent, whereby systemic side effects are managed by preventing the peak plasma level of the pharmaceutically active agent that induces them, while maintaining an effective local level of the pharmaceutically active agent to eradicate tumor cells.

According to an embodiment, the present invention comprises a method for reducing side effects of a local cancer treatment in a patient, wherein the method comprises administering the hydrogel composition of the invention comprising an effective dose of a pharmaceutically active agent, wherein the hydrogel composition is administered intraperitoneally, wherein the side effects are controlled by preventing the peak plasma level of pharmaceutically active agent that induced them while maintaining an effective plasma level of pharmaceutically active agent to eradicate tumor cells.

REFERENCES

Figure 1A:
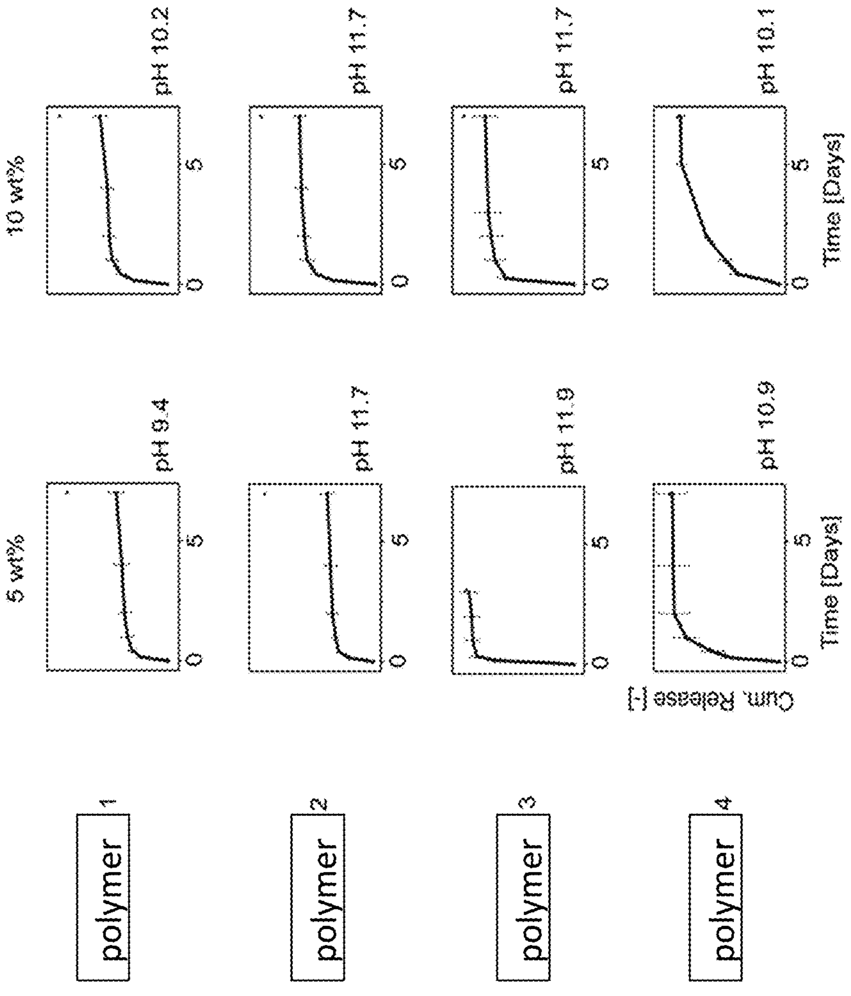
FIGS. 1A/1B shows drug release curves of hydrogel formulations of different polymer designs.

Bakker et al.: Bakker, M. H. et al. Cholesterol Modification of an Anticancer Drug for Efficient Incorporation into a Supramolecular Hydrogel System. Macromol. Rapid Commun. 39, 1800007 (2018)

Bastings et al.: Bastings, M. M. C. et al. A Fast pH-Switchable and Self-Healing Supramolecular Hydrogel Carrier for Guided, Local Catheter Injection in the Infarcted Myocardium. Advanced Healthcare Materials 3, 70-78 (2014)

Ceelen: Ceelen, W. HIPEC with oxaliplatin for colorectal peritoneal metastasis: The end of the road? European Journal of Surgical Oncology 45, 400-402 (2019)

Cho & Kwon: Cho, H. & Kwon, G. S. Thermosensitive poly-(d,l-lactide-co-glycolide)-block-poly(ethylene glycol)-block-poly-(d,l-lactide-co-glycolide) hydrogels for multi-drug delivery. Journal of Drug Targeting 22, 669-677 (2014)

Colin et al.: Colin, P. et al. A Model Based Analysis of IPEC Dosing of Paclitaxel in Rats. Pharm Res 31, 2876-2886 (2014)

Francescutti et al: Francescutti, V. et al. The benefit of intraperitoneal chemotherapy for the treatment of colorectal carcinomatosis. Oncology Reports 30, 35-42 (2013)

Gorecki et al.: Gorecki L, Andrs M, Rezacova M, Korabecny J. Discovery of ATR kinase inhibitor berzosertib (VX-970, M6620): Clinical candidate for cancer therapy. Pharmacol Ther. 2020 June; 210:107518.

Guimarães et al.: Guimarães, C. F., Gasperini, L., Marques, A. P. & Reis, R. L. The stiffness of living tissues and its implications for tissue engineering. Nat Rev Mater 5, 351-370 (2020).

Inaba et al.: Inaba et al. Cancer Chemother. Pharmacol. 1988; 21(3):185-90.

Kiesel et al.: Kiesel B F, Scemama J, Parise R A, Villaruz L, Iffland A, Doyle A, Ivy P, Chu E, Bakkenist C J, Beumer J H. LC-MS/MS assay for the quantitation of the ATR kinase inhibitor VX-970 in human plasma. J Pharm Biomed Anal. 2017 Nov. 30; 146:244-250.

Konno et al.: Konno T, Watanabe J, Ishihara K. Enhanced solubility of paclitaxel using water-soluble and biocompatible 2-methacryloyloxyethyl phosphorylcholine polymers. J Biomed Mater Res A. 2003 May 1; 65(2):209-14

Noh S M.: Measurement of Peritoneal Fluid pH in Patients with Non-Serosal Invasive Gastric Cancer. Yonsei Med J. 2003 February; 44(1):45-48

Ozawa et al.: Ozawa, S., et al. Cell killing action of cell cycle phase-non-specific antitumor agents is dependent on concentration-time product. Cancer Chemother. Pharmacol. 21, (1988)

Posocco et al.: Posocco B, Buzzo M, Follegot A, Giodini L, Sorio R, Marangon E, Toffoli G. A new high-performance liquid chromatography-tandem mass spectrometry method for the determination of paclitaxel and 6α-hydroxy-paclitaxel in human plasma: Development, validation and application in a clinical pharmacokinetic study. PLoS One. 2018 Feb. 23; 13(2)

Wang et al.: Wang L Z, Goh B C, Grigg M E, Lee S C, Khoo Y M, Lee H S. A rapid and sensitive liquid chromatography/tandem mass spectrometry method for determination of docetaxel in human plasma. Rapid Commun Mass Spectrom. 2003; 17(14):1548-52

EXAMPLES

Example 1 Screening of Polymer Library for Suitable Hydrogel Candidates 1.1 Materials and Methods Polymer Synthesis A library of chain extended UPy-PEG polymers was designed and synthesized according to the following procedure:

Telechelic hydroxy terminate poly(ethylene glycol) with a molecular weight of 20 kDa (20.0 gram, 1.0 mmol) was dried at 120° C. in vacuo for 2 hours. Subsequently, 5(2-hydroxyethyl)-6-methyl isocytosine (50HMIC) (338 mg, 2.00 mmol), hexanediisocyanate (1.01 gram, 3.00 mmol), 50 mL dimethylformamide and one drop of dibutyltindilaurate were added to the polymer. The reaction mixture was stirred for 12 hours at 90° C. Subsequently, the reaction mixture was diluted with 50 mL of methanol and poured into 500 mL of diethyl ether. The precipitated polymer was dissolved in 70 mL chloroform and 70 mL methanol and poured into 500 mL diethyl ether. The precipitated polymer was dried in vacuo and obtained as a white solid. SEC (DMF/LiBr, PS-standards): Mn=88 kDa Polymer Design The chain extended UPy-PEG block copolymer comprises a hydrophilic polyethylene glycol chain of MW 10 k or 20 k and increasing amounts of hydrogen bonding UPy (50HMIC) and hydrophobic hard blocks with various degrees of hydrophobicity. Details of the polymers tested are shown in Table 1.

TABLE 1

Properties of UPy-PEG polymers

| Polymer | PEG-chain | Hard block content (#)/PEG-chain | UPy (50 HMIC) (#)/PEG-chain | Type of hard block | Mw kDa | Mn kDa |
|---|---|---|---|---|---|---|
| 1 | 10k | 3 | 2 | Methylene dicyclohexane 4,4-diisocyanate (HDMI) | 114 | 53 |
| 2 | 20k | 2.5 | 1.5 | Methylene dicyclohexane 4,4-diisocyanate (HDMI) | 135 | 80 |
| 3 | 20k | 3 | 2 | Isophorone diisocyanate (IPDI) | 120 | 60 |

TABLE 1-continued

| Properties of UPy-PEG polymers | | | | | | |
|---|---|---|---|---|---|---|
| Polymer | PEG-chain | Hard block content (#)/ PEG-chain | UPy (50 HMIC) (#)/ PEG-chain | Type of hard block | Mw kDa | Mn kDa |
| 4 | 20k | 2.5 | 1.5 | Isophorone diisocyanate (IPDI) | 124 | 76 |
| 5 | 20k | 7 | 5 | Hexane diisocyanate (HDI) | 62 | 32 |
| 6 | 20k | 3 | 2 | Hexane diisocyanate (HDI) | 120 | 88 |
| 7 | 10k | 2.5 | 1.5 | Hexane diisocyanate (HDI) | 48 | 27 |

Hydrogel Formulation

Liquid hydrogel precursor solutions were prepared by dissolving the polymer powder in alkaline PBS having a pH (adjusted by NaOH) of 11.7 or 12.3 and stirring at 70° C. for several hours until dissolved. For a 5 wt. % formulation, 25 mg of polymer powder was dissolved in 475 μl PBS; for a 10 wt. % formulation, 50 mg of polymer powder was dissolved in 450 μl PBS. Qualitative vial inversion tests and macroscopic observations (by eye) were performed to determine the flowability at room temperature. After dissolving the polymer, the pH of the precursor solutions was measured.

Drug Release Experiments

Drug release experiments were performed with a model drug compound: i.e. cholesterol-conjugate of mitomycin C (chol-MMC) (Bakker et al.). This molecule has a strong affinity for the hydrophobic compartments of the hydrogel network and retention of this molecule is a strong indicator for hydrogel network formation as its release is steered by hydrogel erosion. The model drug compound was loaded from a stock solution (30 mM in DMSO) to 0.3 mM in the hydrogel solution. The drug loaded solution (100 μL) was transferred to a Millicell insert, which was placed in a 24-wells plate filled with PBS pH 7.4 (600 μL). Viscous materials were heated to facilitate transfer to the insert. At set time points the PBS was refreshed and the removed PBS was analyzed for drug content by UV absorbance at 363 nm. Release experiments were performed with n=3.

1.2 Results

The requirements for developing a hydrogel that can be administered to a body cavity is that the precursor solution behaves as a liquid at near physiological conditions but responds to an external trigger (change in pH or temperature) to switch to a solid hydrogel material. The flowability of the precursor solutions is determined via a vial inversion test as a visual observation. In this assay, 1 ml of the hydrogel is transferred to a 5 ml vial and its physical state is observed by tube inversion and then it is observed whether the sample flows under its own weight. The flowability and pH of 5 and 10 wt % precursor solutions of the different polymers are listed in Table 2.

TABLE 2

| Results of vial inversions tests of precursor solutions of 5 and 10% formulations of different polymers | | | | |
|---|---|---|---|---|
| | Flowability at RT | | pH precursor solution | |
| Polymer | 5 wt % | 10 wt % | 5 wt % | 10 wt % |
| 1 (Ref) | Does not flow | Does not flow | 9.4 | 10.2 |
| 2 (Ref) | Viscous liquid | Does not flow | 11.7 | 11.7 |
| 3 (Ref) | Does not flow | Does not flow | 11.9 | 11.7 |
| 4 (Ref) | Viscous liquid | Does not flow | 10.9 | 10.1 |
| 5 | Flowing liquid | Viscous liquid | 9.8 | 10.1 |
| 6 | Free flowing liquid | Flowing liquid | 8.8 | 9.6 |
| 7 | Free flowing liquid | Free flowing liquid | 8.2 | 8.8 |

Polymers 1 to 4 are reference polymers, not according to the invention.

Polymers 1 to 4 were very difficult to dissolve as they required harsh conditions (>5 hours stirring at 70° C. using a very alkaline pH 12.3). Vial inversions tests demonstrated that the resulting precursor solutions were too viscous to be handled under physiologically relevant conditions (table 2). For example, polymer 3 (5 and 10 wt %) produced a self-supporting solid at room temperature and very alkaline pH (>11) and only behaved as a liquid after heating to 70 degrees Celsius. Therefore materials based on polymers 1-4 are not suitable for administration into a physiological environment.

Furthermore, these materials produced a burst release of the model drug compound (FIGS. 1A/1B) as a result of the large difference between the pH of the precursor solutions and the switching point of the UPy-moiety (pH 8.5) that drives the sol-gel transition of UPy-PEG materials. Therefore materials based on polymers 1-4 are not suitable as slow release drug depots.

Figure 1B:
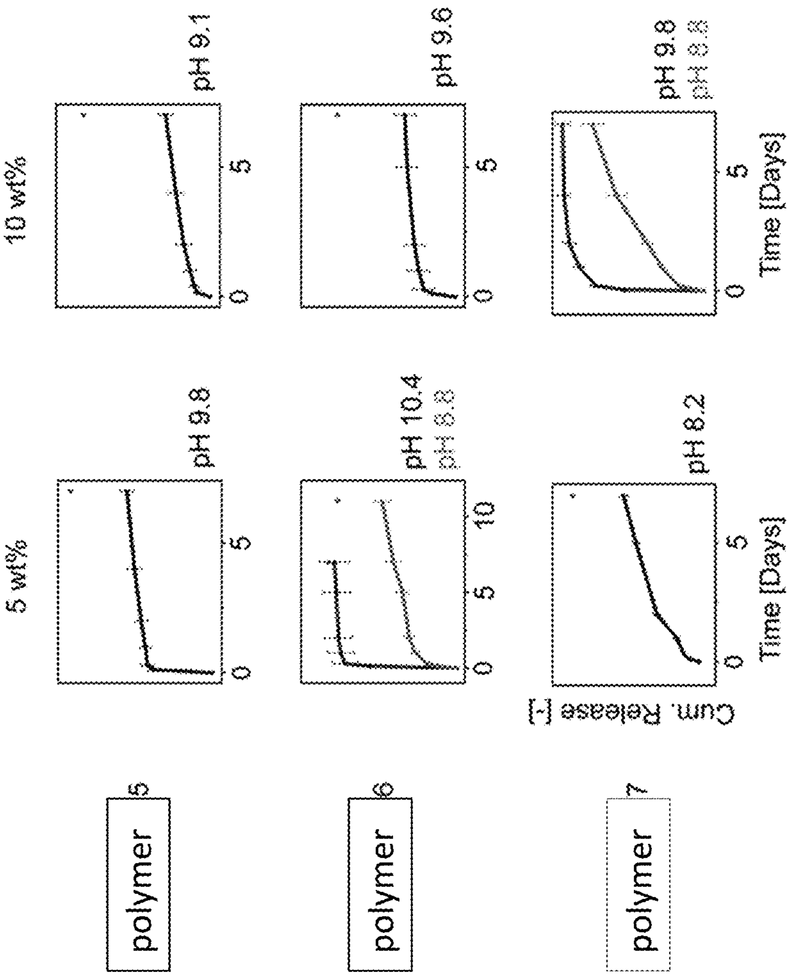

Polymers 5-7 with a less hydrophobic aliphatic hard block display more liquid-like behavior at milder conditions that are closer to physiological conditions. Polymer 5 is liquid at a low polymer density of 5 wt % but is still too viscous at higher polymer densities because the number of hydrophobic hard blocks is higher than in polymers 6 and 7. Polymers 6 and 7 display very liquid-like behavior at physiologically relevant conditions (~pH 9) at low and high polymer density. Additionally, drug release experiments demonstrated that a burst release could be avoided by lowering the pH of the precursor solution closer to physiological conditions and the switching point of the UPy-moiety. This can be seen in FIG. 1 for the 5 wt % formulation of Polymer 6 (pH 10.4→8.8) and the 10 wt % formulation of Polymer 7 (pH 9.8→8.8). During the complete course of the experiment, the hydrogel remains physically stable (as observed by eye) and thereby enables sustained drug release.

1.3 Conclusion

The chain-extended UPy-PEG block copolymer forms a pH-switchable injectable hydrogel under physiologically relevant conditions. The resulting precursor solution behaves as a liquid at slightly alkaline pH (8.5-9.5) but transitions to a solid-like material upon lowering the pH to neutral.

The hydrophobicity of the aliphatic chain in the hard block of the polymer was varied and showed that the ratio of the hydrophobic hard block vs hydrophilic soft block was important for hydrogel formation. Only polymers 5-7 displayed liquid-like behavior at slightly alkaline pH (8.5-9.5). Incorporating more hydrophobic aliphatic hard blocks in the polymer resulted in hydrogel precursor solutions that were unsuitable for administration under physiological conditions. Polymers 6 and 7 were selected for further development of injectable formulations to the peritoneal (body) cavity.

Example 2—Formulation Development of Selected Polymer Candidates 2.1 Materials and Methods Hydrogel Formulation The liquid precursors were prepared by dissolving the polymer powder of polymers 6 and 7 in alkaline PBS (11.7) and stirring at 70° C. for several hours until dissolved. For a 5 wt % formulation, 50 mg of polymer powder was dissolved in 950 μl PBS; for a 6 wt % formulation, 60 mg of polymer powder was dissolved in 940 μl PBS; for a 7 wt % formulation, 70 mg of polymer powder was dissolved in 930 μl PBS. The pH of the precursor solution was adjusted using 1 M NaOH or 1 M HCl.

Rheology

Rotational rheology measurements were performed on an Anton Paar Physica (MCR 501) using a conical (CP-50) plate geometry, with a fixed distance of 0.101 mm. For viscosity measurements, shear viscosity was recorded as function of shear rate (500 to 0.1 s s-1, 10 points per decade, 0.7 s measuring point duration). At lower shear rates (0.1-1 s-1) low torques were measured resulting in unreliable data. 600 μL of liquid hydrogel solution was applied onto the plate of the rheometer. The viscosity of the different materials was measured at 20° C. and 37° C. Measurements were performed in triplicate.

Post Mortem Intraperitoneal Distribution of Different UPy-PEG Formulations Blue-stained hydrogel formulations of polymers 6 (5, 6, and 7 wt %) and 7 (5 and 6 wt %) (total volume 5 ml) were directly administered to deceased surplus rats via an intraperitoneal injection with an 18 G needle. During the 40 minutes after the application of the UPy-PEG hydrogel, the core temperature of the animals was kept warm (around 37 degrees Celsius) and the animals were turned around multiple times, allowing the UPy-PEG hydrogel to distribute optimally through the abdominal cavity. Then, the abdomen was reopened, and the distribution of the gel was assessed by visually inspection.

2.2 Results

Figure 2A:
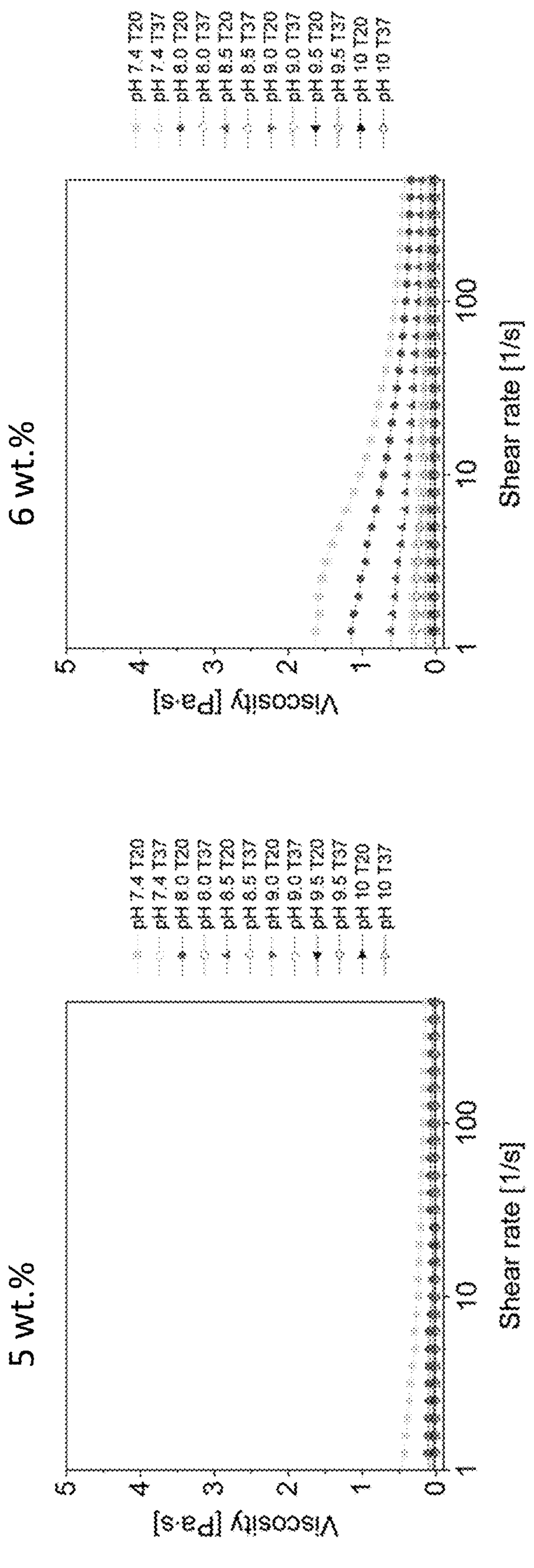
FIGS. 2A/2B/2C shows the viscosity of different hydrogel formulations at various pH and temperatures. Viscosity was recorded as a function of shear rate.
Figure 2B:
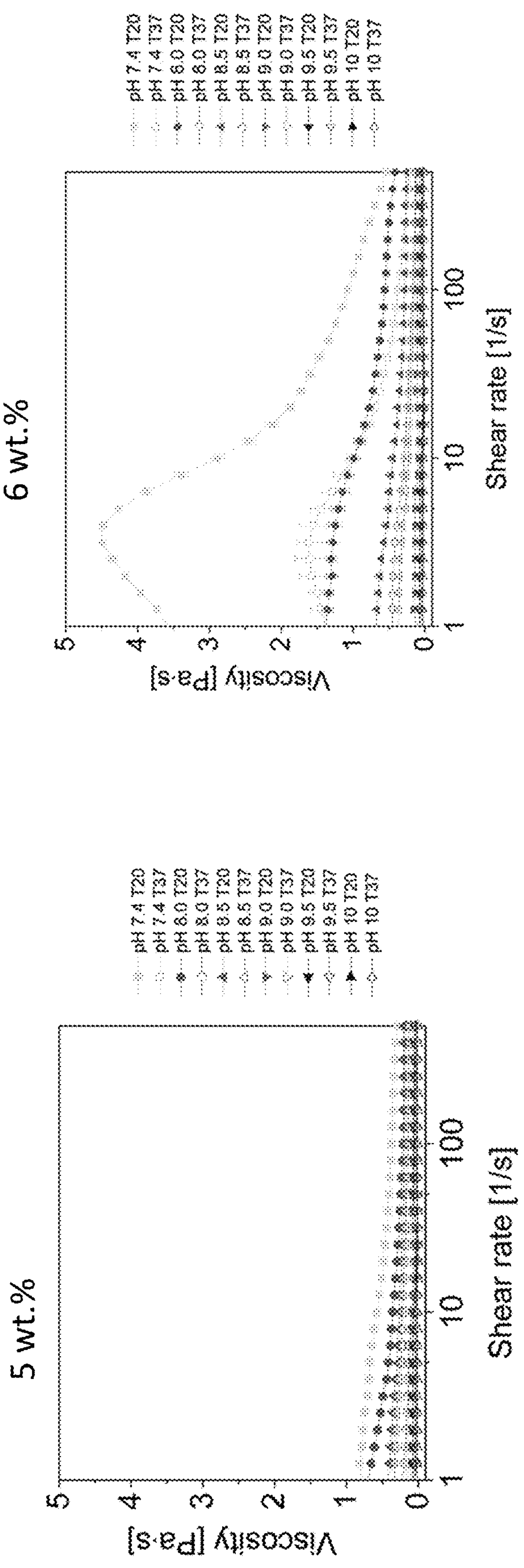
Figure 2C:
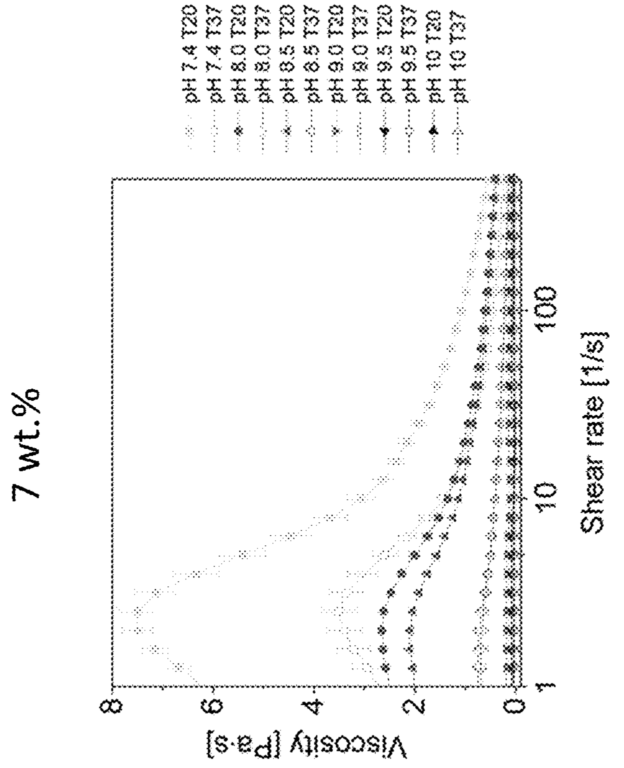

Based on pilot vial inversion tests with hydrogel formulations of various wt % (see example 1) it was hypothesized that 5-10 wt %, hydrogels comprising polymers 6 or 7 would have the desired viscous properties. The viscosity was measured as a function of shear rate for 5, 6 and 7 wt % hydrogels (for polymer 6), and 5 and 6 wt % hydrogels (for polymer 7) at various pH-values ranging from neutral to basic (7.4-10), and temperatures (room and physiological temperature) to determine the sol-gel transition (FIGS. 2A/2B/2C). All formulations with a pH≥9.0 have a constant viscosity at all shear rates displaying Newtonian behavior where the material flows as a liquid. Upon lowering the pH to 8.5 and lower to physiological conditions, the sol-gel transition is reached where the viscosity increases, especially for the 6 and 7 wt % hydrogels. At these pH-values the hydrogels behave as shear-thinning non-Newtonian media with increased viscosity for higher wt % hydrogels.

The viscous properties of the different formulations as determined by rheometry are consistent with the results of post mortem intraperitoneal administration of the hydrogel in rats. Hydrogel solutions with a low viscosity and Newtonian behavior due to a low polymer density, behaved as liquids (polymer 7, 5 wt %). They flowed freely in the peritoneal cavity but did not form a stable gel. On the other hand, hydrogel solutions with a high viscosity and non-Newtonian behavior due to a high polymer density (polymer 6 and 7, 7 wt %), were too viscous to distribute uniformly in the peritoneal cavity and formed patches of solid gel.

In between there was a sweet spot with the optimal viscosity and sol-gel transition to enable uniform distribution in the peritoneal cavity and stable gel formation. This was especially true for the (polymer 6) that also adhered to the parietal peritoneum.

2.3 Conclusion

Polymer 6, 6 wt % hydrogel formulation combines good viscous properties (for administration as liquid) and sol-gel transition point (for stable) gel formation in in the (body) peritoneal cavity.

Example 3—Drug Loading Capacity of UPy-PEG Hydrogels 3.1 Materials and Methods

Hydrogel Formulation

The liquid hydrogel precursors were prepared by dissolving the polymer powder of polymers 6 and 7 in alkaline PBS (pH 11.7) and stirring at 70° C. for several hours until dissolved. For a 5 wt % formulation, 50 mg of polymer powder was dissolved in 950 μl PBS; for a 7 wt % formulation, 70 mg of polymer powder was dissolved in 930 μl PBS. for a 8 wt % formulation, 80 mg of polymer powder was dissolved in 920 μl PBS. The pH of the precursor solution was adjusted using 1 M NaOH or 1 M HCl. The pH of the precursor solutions obtained is shown in Table 3.

Drug Release Experiments

Drug release experiments were performed with the model drug compound: i.e. cholesterol-conjugate of mitomycin C (chol-MMC). This molecule has a strong affinity for the hydrophobic compartments of the hydrogel network and retention of this molecule is a strong indicator for hydrogel network formulation. The model drug compound was loaded from a stock solution (30 mM in DCM) to 3 or 6 mM in the hydrogel solution. The organic solvent was removed by evaporation. The drug loaded solution (100 μL) was transferred to a Millicell insert, which was placed in a 24-wells plate filled with PBS pH 7.4 (600 μL). At set time points the PBS was refreshed and the removed PBS was analyzed for drug content by UV absorbance at 363 nm. Release experiments were performed with n=3.

3.2 Results

The pH of the precursor solutions obtained is shown in Table 3.

TABLE 3

| Polymer | pH precursor solution 5 wt % | 7 wt % | 8 wt % |
|---|---|---|---|
| 6 | 8.1 | 8.9 | 8.8 |
| 7 | 7.9 | 8.7 | |

Figure 3A:
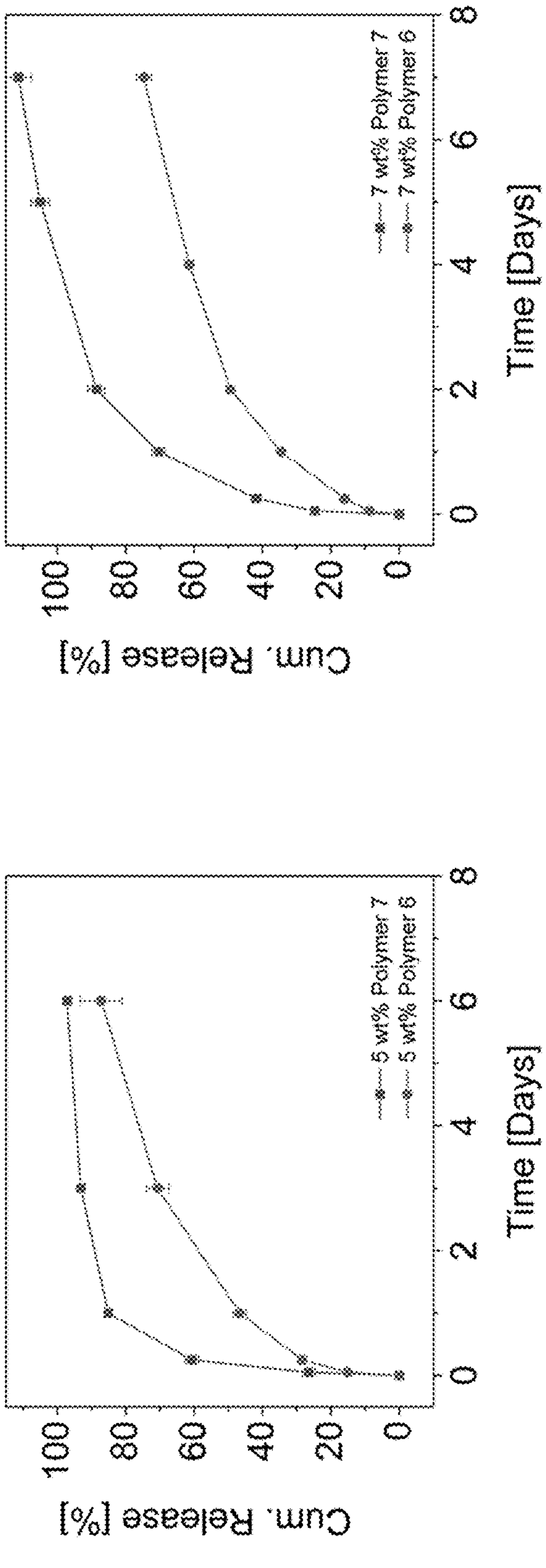
FIGS. 3A/3B show cumulative release of 3 mM (FIG. 3A) and 6 mM (FIG. 3B) chol-MMC from 5 different polymer solutions.
Figure 3B:
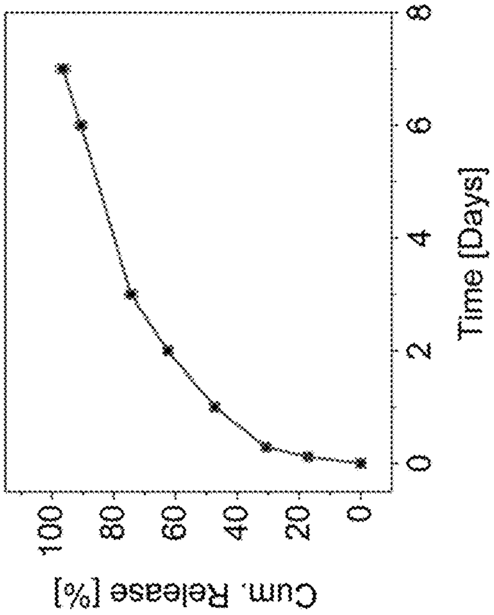

A direct comparison in drug loading capacity was made between polymer 6 and 7. For both 5 wt % and 7 wt % hydrogel formulations, a 3 mM drug loading resulted in different release kinetics between the polymer 7 and polymer 6 hydrogel systems (FIG. 3A). The hydrogel of polymer 7 showed a more burst-like release, combined with rapid dissolution of the hydrogel. Here, the high concentration of hydrophobic model drug compound destabilized the hydrophobic compartments of the hydrogel network resulting in a poor performance. Polymer 6, on the other hand, formed a more stable hydrogel with a sustained drug release. Moreover, there was a significant difference in the pH of the 7 wt % precursor solution. The precursor solution of Polymer 6 had a pH that was still the above the sol-gel transition; this means that pH-switching behavior was not compromised. The hydrogel of polymer 7 already behaved as viscous liquids at lower pH-values due to the higher drug loading. Even higher drug loadings of 6 mM could be obtained by using a 8 wt % formulation of Polymer 6 (FIG. 3B). These results demonstrate that polymer 6 forms more robust hydrogel systems due to the greater hydrophobic block content and longer polymer chain length, resulting in more and robust physical crosslinks.

3.3 Conclusion

Hydrogels based on the polymer 6 are more robust and have a higher drug loading capacity. Results from example 2 also demonstrate that the viscous properties of polymer 6 result in a better peritoneal distribution. The polymer 7 is an alternative for situations where more liquid properties at lower pH are required.

Example 4—Drug Release in Simulated Peritoneal Fluid With Elevated pH

4.1 Materials and Methods

Hydrogel Formulation

The tested hydrogel precursor solution was polymer 6, 6 wt % in PBS as described in Example 2.

Drug Release Experiments

The model drug compound was loaded from a stock solution (30 mM in DMSO) to 0.3 mM in the precursor solution. The drug loaded solution (100 μL) was transferred to a Millicell insert, which was placed in a 24-wells plate filled with PBS pH 7.4, 7.8 or 8.2 (600 μL). At set time points the PBS was refreshed and the removed PBS was analyzed for drug content by UV absorbance at 363 nm. Release experiments were performed with n=3.

4.2 Results

Figure 4:
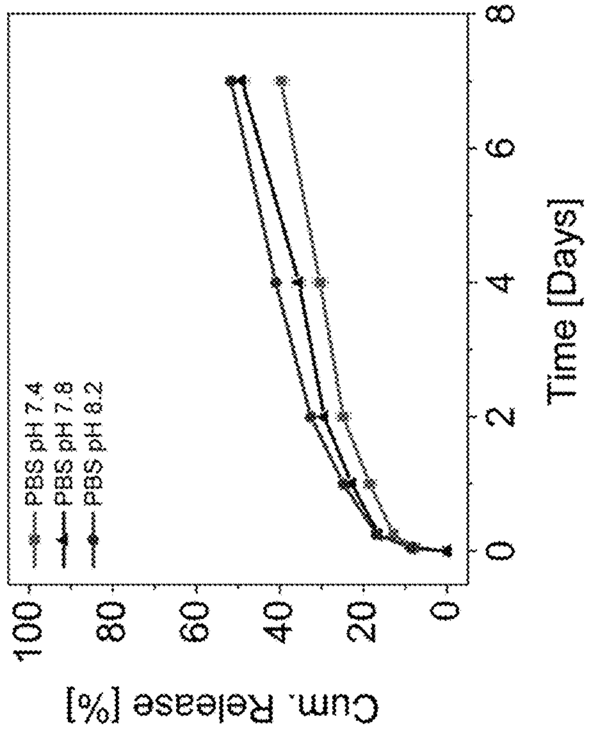
FIG. 4 shows the cumulative release of 0.3 mM chol-MMC into simulated peritoneal fluid with pH 7.4, 7.8 and 8.2.

The pH of peritoneal fluid ranges between 7.5 and 8.0 and contains significant buffering capacity (Noh SM). In view of the pH-sensitivity of UPy-PEG hydrogel systems, it is important to test the influence of this slightly alkaline physiological fluid on the stability of the hydrogel and consequent release kinetics. The peritoneal fluid was simulated using PBS with a pH of 7.4, 7.8 and 8.2. Small differences in release kinetics (FIG. 4) were found where the highest pH disrupted the hydrogel network most, result in the highest release of model drug compound.

4.3 Conclusion

The polymer 6-based hydrogel remains stable and can sustain a prolonged drug release in the slightly alkaline environment of simulated peritoneal fluid.

Example 5—UPy-PEG Hydrogel Formulations for the Sustained Delivery of Taxanes

5.1 Materials and Methods

Hydrogel Formulations

The tested hydrogel formulation was the polymer 6, 6 wt % in PBS as described in Example 2.

Hydrogel-Drug Formulations

Stock solutions (50 mg/ml) of docetaxel (MW 807 g/mol) or paclitaxel (MW 854 g/mol) were prepared in DMSO. A small volume of the stock solution was added to the liquid precursor solution at pH 9 to arrive at a drug-loaded precursor solution containing 0.2 mM or 0.16-0.17 mg/ml of taxane. The solution (100 μL) was transferred to a Millicell insert, which was placed in a 24-wells plate filled with PBS pH 7.4 (600 μL). At set time points the PBS was refreshed and the removed. PBS was analyzed for drug content via HPLC-MS/MS. Release experiments were performed with n=3.

Quantification of Docetaxel or Paclitaxel Concentrations in Release Medium

Quantification of docetaxel or paclitaxel concentration in release sample was performed using a HPLC tandem mass spectrometry method (Posocco et al., Wang et al.).

5.2 Results

Figure 5:
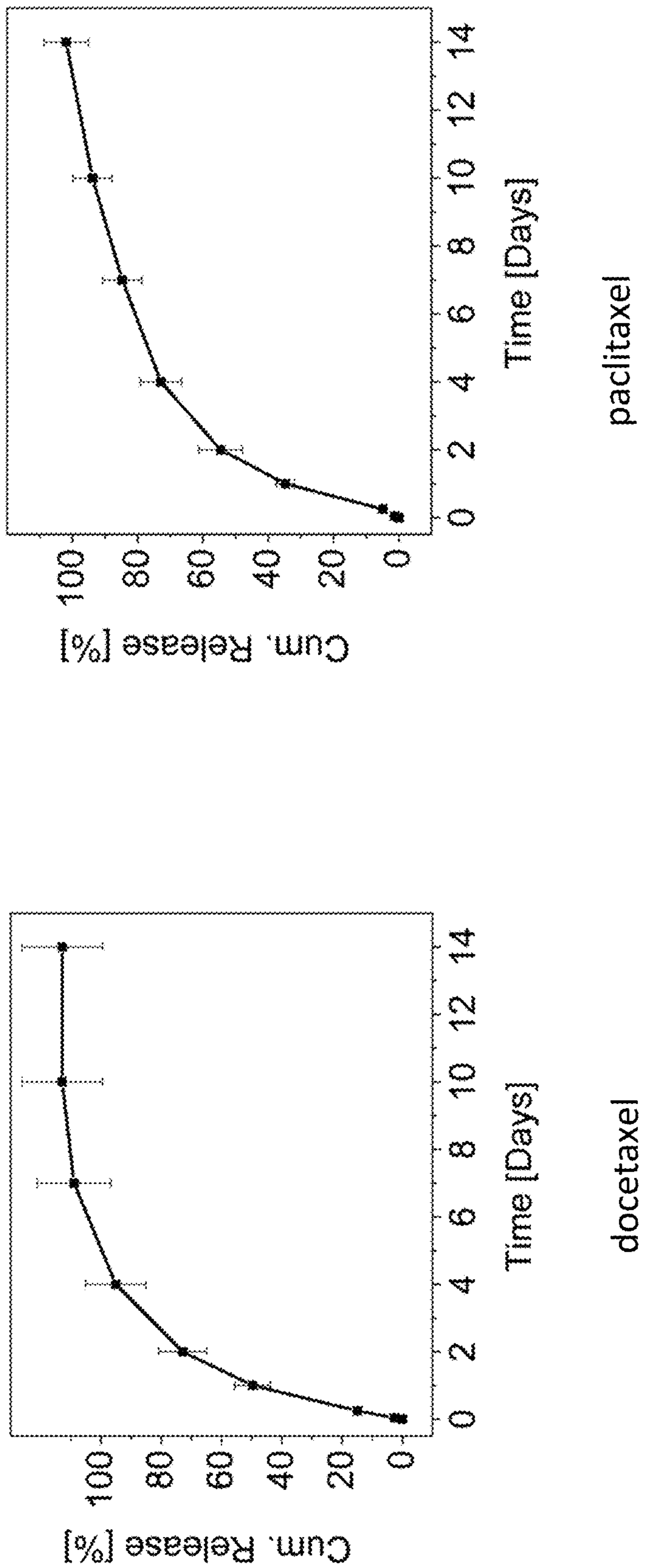
FIG. 5 shows the cumulative release of docetaxel (5A) and paclitaxel (5B).

Hydrogels consisting of polymer 6 were considered good candidates for further development as controlled drug delivery platforms. In vitro drug release experiments using hydrogel-drug formulations were performed to produce a good understanding of the molecular interactions between drug compounds and the hydrogel network. Taxanes (such as docetaxel and paclitaxel) are very hydrophobic cytotoxic compounds that are commonly used for (intraperitoneal) chemotherapy. Due to their high hydrophobicity these compounds are, in general, formulated together with non-ionic surfactants such as Cremophor (paclitaxel) or emulsifiers such as polysorbate (docetaxel) ton increase drug solubility. However, these additives are often associated with additional toxicity or hypersensitivity. Taxanes exert their anti-cancer effect by inhibiting the mitotic spindle—they bind to the microtubules and prevent their depolymerization, thus inhibiting mitosis and inducing apoptosis in cells undergoing the division process. The drugs are cell-cycle specific in the M-phase. In most animal cells, the M-phase takes only about an hour—a small fraction of the total cell-cycle time, which often lasts 12-24 hours. To realize an adequate drug exposure to exert a cytotoxic effect, malignant cells should be exposed to the drug for several cell cycles. FIG. 5 demonstrates that UPy-PEG formulations of taxanes can enable a sustained drug release for 1 to 2 weeks, sufficient to cover several cell cycles. Furthermore, no irritating or toxic additives were needed to help solubilize the hydrophobic drug compounds as they are retained in the hydrophobic compartments of the hydrogel network. The drug loaded hydrogels were transparent, indicating that drug compounds were successfully solubilized in the hydrogel network at higher concentrations (0.16-0.17 mg/ml) than the solubility of taxanes in water (0.1 μg/ml) (Konno et al.).

5.3 Conclusion

UPy-PEG hydrogels can be used as effective formulation vehicle to solubilize highly hydrophobic drug compounds and prolong drug exposure.

Example 6—UPy-PEG Hydrogel Formulations for the Sustained Delivery of Mitomycin C

6.1 Materials and Methods

Hydrogel Formulations

The tested hydrogels were the polymer 6, 6, 7 and 8 wt % in 0.9% saline. For a 6 wt % formulation, 60 mg of polymer powder was dissolved in 940 μl 0.9% saline; for a 7 wt % formulation, 70 mg of polymer powder was dissolved in 930 μl PBS. for a 8 wt % formulation, 80 mg of polymer powder was dissolved in 920 μl 0.9% saline. The pH of the precursor solution was adjusted to 8.5, 9.0 or 9.5 for each of the concentrations using 1 M NaOH or 1 M HCl.

Drug Release Experiments

Mitomycin C was loaded from a stock solution (52 mM in DMSO) to 0.52 mM in the hydrogel solution. The drug loaded solution (100 μL) was transferred to a Millicell insert, which was placed in a 24-wells plate filled with PBS pH 7.4 (600 μL). At set time points the PBS was refreshed and the removed PBS was analyzed for drug content UV absorbance at 363 nm. Release experiments were performed with n=3.

6.2 Results

Figure 6:
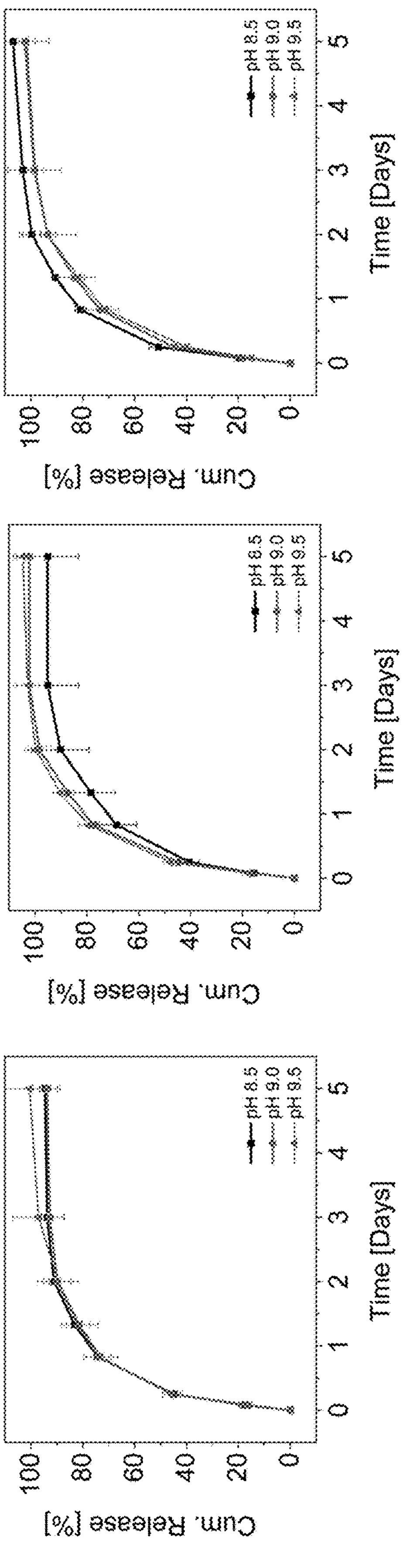
FIG. 6 shows the cumulative release of mitomycin C from hydrogels. The pH of the liquid precursor solutions was 8.5, 9.0 or 9.5 prior to starting the release experiment.

Hydrogels containing polymer 6 were considered good candidates for further development as controlled drug delivery platforms. In vitro drug release experiments using hydrogel-drug formulations were performed to produce a good understanding of the molecular interactions between drug compounds and the hydrogel network. Mitomycin C is a cytostatic antibiotic and is commonly used in (intraperitoneal) chemotherapy. It has good solubility in water (1 mg/ml) and can be readily dissolved in physiological media for intravesical instillation or HIPEC-procedures. Mitomycin is an alkylating drug, meaning it inhibits the transcription of DNA into RNA, stopping protein synthesis and taking away the cancer cell's ability to multiply. The cytotoxic effect is AUC-dependent, meaning that it depends on the value of concentration x exposure time or the area under the drug concentration-time curve (AUC) (Inaba et al.). In intravesical instillation, or HIPEC-procedures the exposure to mitomycin C is limited to 1-2 hours. Therefore, also in view of the AUC-dependent cell killing action, if the drug exposure can be extended to 1-2 days, the efficacy of the drug can be augmented 20-50 times. Several UPy-PEG formulations of polymer 6 were tested, all demonstrating the potential to sustain a mitomycin C release of 1-2 days. The results are shown in FIG. 6. The drug release is not dependent on the polymer density, as formulations of 6, 7 or 8 wt % displayed similar kinetics. This result indicates that in this case drug release is not due to erosion, but instead is diffusion-controlled due to the hydrophilicity of mitomycin C. Drug-loaded hydrogel precursor solutions with various pH-values were prepared to study the effect of the sol-gel transition on the burst drug release. More liquid solutions with a higher pH did not give rise to an increased burst release of mitomycin C. This means that the viscosity of the injectable solution can be tuned independently without compromising the kinetics of drug release. It is expected that other hydrophilic drugs or chemotherapeutics (such as 5-fluorouracil, oxaliplatin, cisplatin, carboplatin or gemcitabine) can be formulated in the hydrogel system as well.

6.3 Conclusion

UPy-PEG hydrogels can be used as effective formulation vehicles to prolong the drug exposure of highly hydrophilic drug compounds

Example 7—UPy-PEG Hydrogel Formulations for the Sustained Delivery of Combination Therapy

7.1 Materials and Methods

Hydrogel Formulations The tested hydrogel was Polymer 7, 5 wt % in PBS as described in Example 2.

Drug Release Experiments

Mitomycin C (MMC) was loaded from a stock solution (52 mM in DMSO) to 0.52 mM in the hydrogel solution. VX970 was loaded from a stock solution (1.2 mg/ml in DMSO) to 12 μg/ml. The drug loaded solution (100 μL) was transferred to a Millicell insert, which was placed in a 24-wells plate filled with PBS pH 7.4 (700 μL). At set time points the PBS was refreshed and the removed PBS was analyzed for MMC content by UV absorbance at 363 nm. For VX970, a HPLC-MS/MS method was used (Kiesel et al.). Release experiments were performed with n=3.

7.2 Results

Figure 7:
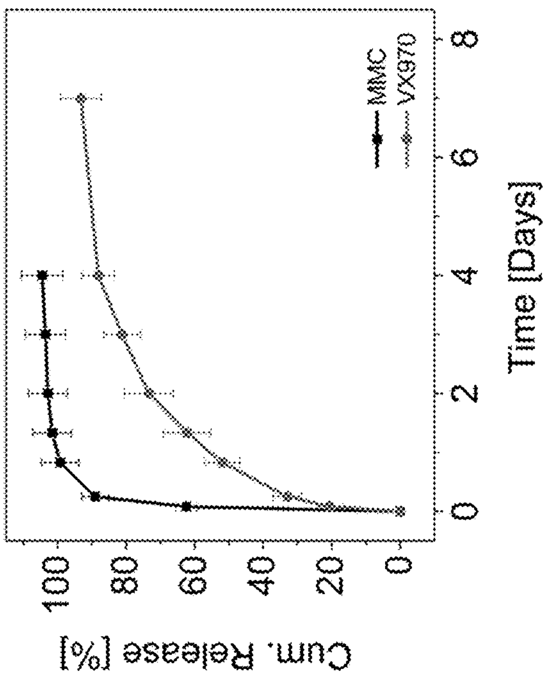
FIG. 7 shows the cumulative release of mitomycin C and VX970 from a hydrogel.

Also, hydrogels consisting of polymer 7 can be considered a good candidate for further development as controlled drug delivery platforms. In vitro drug release experiments using hydrogel-drug formulations of two drug compounds combined (MMC and VX-970) were performed to produce a good understanding of the molecular interactions between drug compounds and the hydrogel network. Mitomycin is an alkylating drug, causing DNA damage. VX-970 (berzosertib) (Gerecki et al.) is a clinical stage potent and selective inhibitor of ATR, replication checkpoint kinase. VX-970 has anti-proliferative qualities as a single agent, but also increases the efficacy of DNA-damaging drugs, without additional toxicity. Whereas mitomycin is soluble in water (1 mg/ml), VX-970 is insoluble in water due to its hydrophobic structures. Similar to taxanes, UPy-PEG hydrogels can be used to help solubilize VX-970 without the use of additives such as DMSO or PEG400. Due to the hydrophobic nature of the molecule and consequent affinity with the hydrophobic compartments of the hydrogel, VX-970 is released slower than MMC (FIG. 7). The different release kinetics of MMC and VX-970 enable a synergetic sequential combination therapy where DNA damage is initially caused by the alkylating effect of MMC, followed by the inhibition of DNA-repair mechanisms by VX-970.

7.3 Conclusion

UPy-PEG hydrogels can be used as effective formulation vehicles to enable sequential combination therapies of multiple drug compounds.

Example 8—Injectability of UPy-PEG Hydrogels With Catheter or Pipette 8.1 Materials and Methods Hydrogel Formulations The tested hydrogels were Polymer 6: 6, 7 and 8 wt % in PBS. The liquid hydrogel precursors were prepared by dissolving the polymer powder in alkaline PBS (pH 11.7) and stirring at 70° C. for several hours until dissolved. For a 6 wt % formulation, 600 mg of polymer powder was dissolved in 9400 μl PBS; for a 7 wt % formulation, 700 mg of polymer powder was dissolved in 9300 μl PBS. for a 8 wt % formulation, 800 mg of polymer powder was dissolved in 9200 μl PBS. The pH of the precursor solution was adjusted to 9.0 or 9.5 for each of the concentrations using 1 M NaOH or 1 M HCl.

Rheology

Rotational rheology measurements were performed on an Anton Paar Physica (MCR 501) using a conical (CP-50) plate geometry, with a fixed distance of 0.101 mm. For viscosity measurements, shear viscosity was recorded as function of shear rate (500 to 0.1 $s^{-1}$; 10 points per decade; 38 measuring points; varying measuring point duration log 10→1). At lower shear rates (0.1-1 $s^{-1}$), low torques were measured resulting in unreliable data. 600 μL of liquid hydrogel solution was applied onto the plate of the rheometer. The viscosity of the different materials was measured at 20° C.

Injectability

The injectability was tested using a standard 1 ml micropipet and standard 1 ml pipette tips. The solution was considered injectable if the liquid could be drawn into and expelled out of the pipette tip. Another injectability test was performed using a 40 cm long, 14 CH catheter with hydrophilic coating. Syringes (10 ml) were loaded with the hydrogel solutions and connected to the luer lock connection of the catheters. Hydrogel solutions were considered injectable if a continuous stream of fluid exited the catheter fenestrations.

8.2 Results

Figure 8:
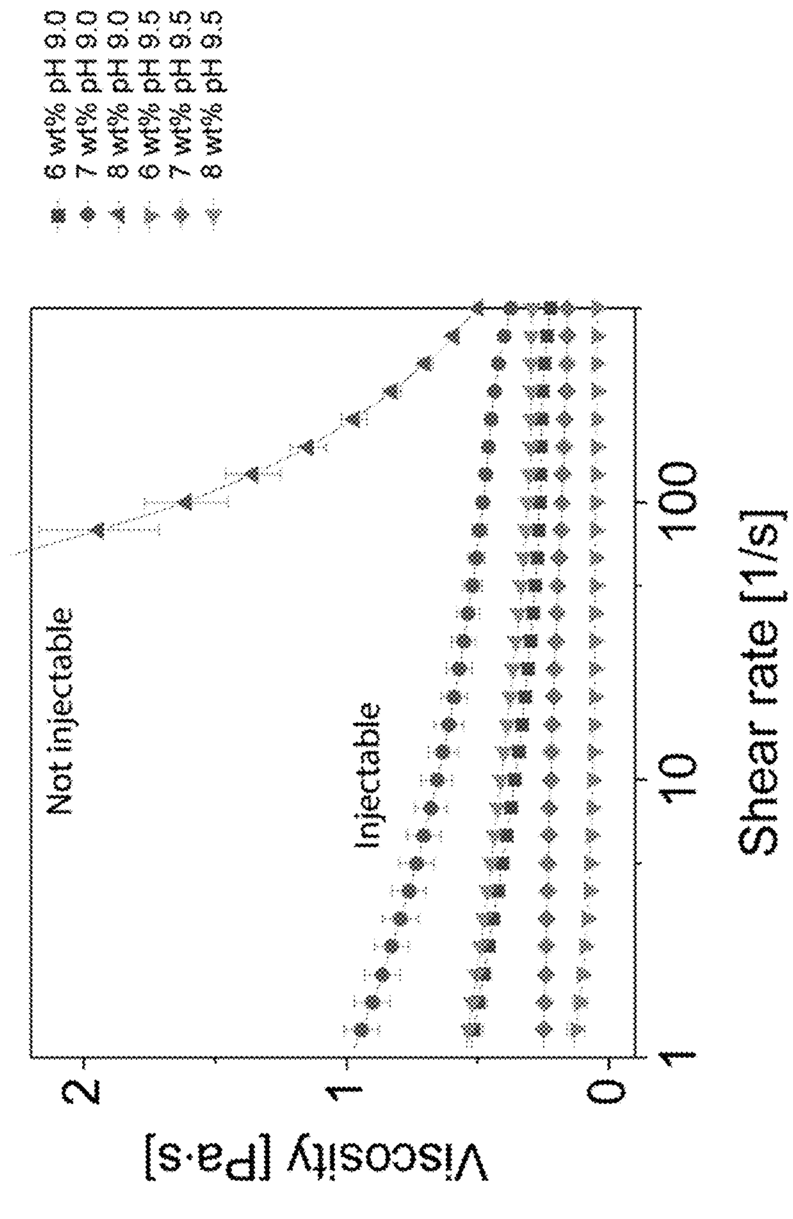
FIG. 8 shows the relationship between administrability and viscosity of polymer 6, 6, 7 or 8 wt % at pH 9.0 or 9.5.

The viscosity of the liquid precursor solutions strongly depends on polymer density and pH (FIG. 8). An increase in polymer density results in a higher viscosity. At pH 9.0, the 6 wt % formulations displays slight non-Newtonian behavior, whereas the 7 and 8 wt % formulations display more pronounced non-Newtonian behavior. Injectability tests with micropipette and catheter demonstrated that the viscous properties of the 8 wt % formulation at pH 9 impeded injectability. The viscosity of the formulations can be tuned by increasing the pH to 9.5. Importantly, at pH 9.5 the 8 wt % formulation could again be handled as a liquid with lower viscosity and less pronounced non-Newtonian behavior. The 6 and 7 wt % formulations at pH 9.5 behaved as Newtonian liquids with low viscosity that is constant for all shear rates.

8.3 Conclusion

The viscosity of liquid hydrogel solution can be tuned by changing the polymer density and pH to facilitate administration via catheter.

Example 9—Soft Elastic Modulus of UPy-PEG Hydrogels 9.1 Materials and Methods

Hydrogel Formulations

The tested hydrogel was polymer 6, 6, wt % in PBS with pH 7.4.

Rheology

Oscillatory rheology measurements were performed on an Anton Paar Physica (MCR 501) using a conical (CP-50) plate geometry, with a fixed distance of 0.101 mm. For frequency sweep measurements, storage and loss moduli were recorded as function of frequency (0.1-100 rad $s^{-1}$, 10 points per decade, strain=1%). 600 μL of hydrogel was applied onto the plate of the rheometer. The storage and loss moduli were measured in triplicate at physiological temperature, 37° C.

9.2 Results

Figure 9:
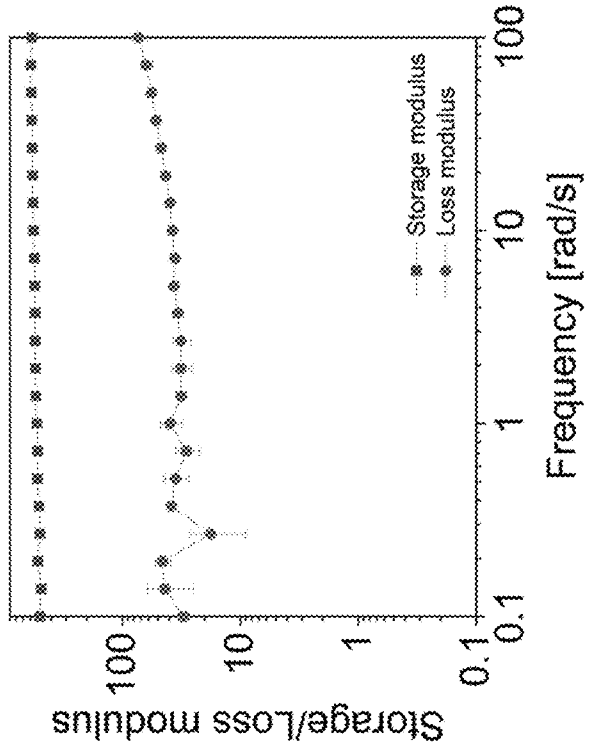
FIG. 9 shows a frequency sweep of polymer 6, 6 wt, pH 7.4 in PBS, recorded at 37° C.

Rheological characterization was performed at 37° C., and with the pH of the hydrogel at 7.4 to simulate physiological conditions after administration to a body cavity. As shown in FIG. 9, the storage modulus had a constant value of 500-600 Pa for all frequencies. The loss modulus was significantly lower (30-50 Pa) than the storage modulus demonstrating that the material behaves more as an elastic solid. The recorded storage modulus is lower than the elastic modulus of tissue organs that are present in the peritoneal cavity, such as pancreas (2.9 kPa), liver 4.0-6.5 kPa) (Guimarães et al.).

9.3 Conclusion

At physiological conditions, the UPy-PEG polymer forms a soft elastic hydrogel.

Example 10—In Vivo Safety of Intraperitoneal Administration of UPy-PEG Hydrogel 10.1 Materials and Methods Hydrogel Formulations The tested hydrogel formulation was polymer 6, 6 wt % in PBS with a pH of 9.0 of the precursor solution that was administered to the animals by injection.

In Vivo Safety Testing

Eighteen male and female healthy WAG/Rij rats of 10-16 weeks of age weighting 140-260 grams were purchased from a registered breeding company (Charles River Laboratories, Calco, Italy) and socially housed in a temperature- and humidity-controlled room with 12-hour light/dark cycles. the UPy-PEG hydrogel was administered via a single i.p. injection at a volume-to-body weight ratio of 20 ml/kg, corresponding to 3-5 ml hydrogel. Animals were euthanized after a follow-up of 14 or 28 days.

Biochemical Analysis

At the necropsy, serum was collected and serum parameters for liver- and kidney damage and function were examined, including alanine transaminase (ALT), aspartate transaminase (AST), alkaline phosphatase (ALP), and estimated glomerular filtration rate (eGFR). In addition, electrolyte balance, inflammation parameters, and parameters for bone marrow functioning were determined.

Histopathology

For histopathological examination, several organs including the liver, kidney, duodenum, spleen, and (mesenteric) lymph nodes were resected, carefully inspected, and fixed in a 4% formaldehyde solution. After embedding in paraffin, 5 μm thick tissue sections were cut and subjected to hematoxylin-eosin (H&E) staining. Each section was scored 0 (no vacuolated macrophages), 1 (vacuolated macrophages are minimally present), 2 (vacuolated macrophages are mildly present), 3 (vacuolated macrophages are moderately present), or 4 (large clusters of vacuolated macrophages).

10.2 Results

At necropsy, the animals were visually examined at 14 days (n=3) and 28 days (n=10) and showed no signs of residual UPy-PEG hydrogel or tissue abnormalities—e.g. peritonitis (puss, redness), surface damage to organs, or abdominal adhesions. Markers of kidney, liver, and bone marrow functioning, presence of hepatotoxicity and inflammation, and electrolyte balance were determined in blood and displayed in Table 4. Thrombocyte count was significantly lower in the UPy-PEG hydrogel group after 28 days compared to the control group and the UPy-PEG hydrogel group sacrificed at day 14. For all other parameters, no significant differences were found between the groups.

TABLE 4

Biochemical parameters of the animals in the control and experimental group.

| | PBS Day 14 | UPy-PEG hydrogel Day 14 | UPy-PEG hydrogel Day 28 |
|---|---|---|---|
| Liver function and damage | | | |
| AST (U/l) | 131.0 (37.0) | 119.3 (34.0) | 120.4 (30.7) |
| ALT (U/l) | 69.5 (5.1) | 57.5 (10.5) | 76.9 (42.5) |
| ALP (U/l) | 151.8 (35.9) | 86.1 (20.8) | 145.1 (19.6) |
| γ-GT (U/l) | <3 | <3 | <3 |
| Albumin (g/l) | 16.5 (2.1) | 14.4 (1.0) | 14.9 (0.9) |
| Kidney function | | | |
| eGFR (ml/min/1.73 $m^2$) | 82.9 (6.7) | 86.1 (4.9) | 85.0 (3.8) |
| Inflammation | | | |
| CRP (mg/l) | <1 | <1 | <1 |
| Haptoglobin (g/l) | 0.1 (0.014) | 0.1 (0.024) | 0.1 (0.024) |
| Electrolytes | | | |
| Sodium (mmol/l) | 144.8 (3.6) | 144.8 (1.0) | 142.8 (1.1) |
| Potassium (mmol/l) | 5.5 (0.3) | 4.8 (0.6) | 4.9 (0.7) |
| Bone marrow functioning | | | |
| Hemoglobin (mmol/l) | 8.9 (0.4) | 8.4 (0.5) | 8.5 (0.4) |
| Leukocytes ($10^9$/l) | 4.9 (0.8) | 4.7 (0.8) | 4.2 (0.7) |
| Thrombocytes ($10^9$/l) | 998.0 (43.8) | 842.0 (174.0) | 724.4 (363.0) |

Abbreviations: AST, aspartate aminotransferase; ALT, alanine aminotransferase; ALP, alkaline phosphatase; γ-GT, glutamyl transpeptidase; eGFR, estimated glomerular filtration rate; CRP, c-reactive protein.

Histopathological changes in intra-abdominal organs were examined and scored in experimental animals on days 14 and 28 after UPy-PEG administration and in control animals on day 14 after PBS administration (5, Table 5). vacuolated (resident) macrophages with foreign material were found in several organs in the peritoneal cavity. In the kidney, vacuolated macrophages were most often found in the glomeruli and remained stable in number over time.

TABLE 5

Histopathological scoring of histopathological tissues

| | PBS Day 14 | UPy-PEG hydrogel Day 14 | UPy-PEG hydrogel Day 28 |
|---|---|---|---|
| Degree of vacuolated macrophages | | | |
| Liver | 0 | 1.8 (0.5) | 2.3 (0.9) |
| Duodenum | 0 | 0 | 1.11 (1.4) |
| Fat and mesentery | 0 | 2.33 (0.6) | 1.9 (1.1) |
| Kidney | 0 | 2.3 (0.6) | 2.6 (0.6) |
| Spleen | 0 | 4.0 (0) | 2.5 (1.2) |
| Colon | 0 | 0 | 0 |
| Pancreas | 0 | 0 | 0 |
| Degree of steatosis | | | |
| Liver | 0 | 1.5 (0.6) | 0.5 (1.1) |

10.3 Conclusion

In vivo administration of the UPy-PEG hydrogel showed no macroscopic adverse effects after injection in the peritoneal cavity of rats. However, vacuolated macrophages were detected in gastrointestinal tissues 28 days after administration. Importantly, the applicants showed that the UPy-PEG hydrogel is safe, feasible, and tolerated in healthy rats.

Example 11—UPy-PEG Hydrogel Formulations for the Sustained Delivery of TLR-Agonists 11.1 Materials and Methods Hydrogel Formulations The tested hydrogels were Polymer 6, 6 & 10 wt % in PBS as described in Example 2.

Drug Release Experiments

The TLR-agonist resiquimod (synonym R848) was loaded from a stock solution (50 mM in DMSO) to 1.27 mM in the hydrogel. The TLR-agonist telratolimod (synonym MEDI9197) was loaded from a stock solution (10 mM in DMSO) to 0.5 mM in the hydrogel.

The drug loaded solution (100 μL) was transferred to a Millicell insert, which was placed in a 24-wells plate filled with PBS pH 7.4 (700 μL). At set time points the PBS was refreshed and the removed PBS was analyzed for R848 content UV absorbance at 320 nm. For MEDI9197, PBS was substituted for a volatile ammonium carbonate buffer and a HPLC-MS method was used. Release experiments were performed with n=3.

11.2 Results

In vitro drug release experiments using hydrogel-drug formulations of two different TLR-agonists (R848 and MEDI9197) were performed to produce a good understanding of the molecular interactions between drug compounds and the hydrogel network. Both compounds are TLR-agonists that are potent activators of the immune system by converting the immunosuppressive environment of tumors into an immunoactive environment through cytokine secretion and activation of cytotoxic lymphocytes. TLR-agonists can remodel the tumor microenvironment and reprogram the host response, promoting antitumor immunity. However, the widespread application of TLR-agonists is hampered by severe toxic side effects caused by systemic and nonspecific immune responses leading to a cytokine storm. To overcome this problem, delivery of TLR-agonists needs to be localized to the disease area (e.g. peritoneal cavity) to improve the safety and effectiveness of this immune therapy.

Figure 11A:
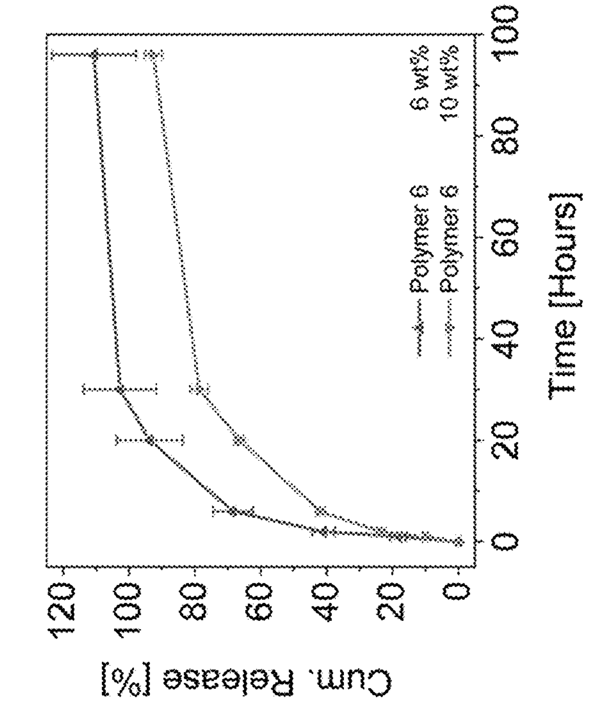
FIGS. 11A/11B show the cumulative release of TLR-agonist R848 (FIG. 11A) and TLR-agonist MED19197 (FIG. 11B) from 6 and 10 wt. % hydrogel formulations.
Figure 11B:
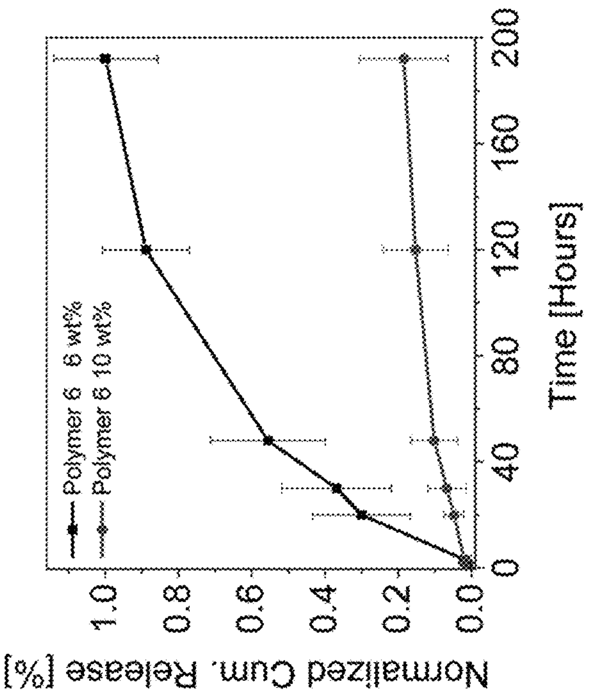

TLR-agonist R848 is relatively hydrophilic and most of the drug is released within 24 hours (FIG. 11A). TLR-agonist MEDI9197 is relatively hydrophobic due to due to its long alkyl tail. Due to the hydrophobic nature of the molecule and consequent affinity with the hydrophobic compartments of the hydrogel, MEDI9197 is released slower than MMC (FIG. 11B). The different release kinetics of these TLR-agonists can be used to control the timing of, and localize the therapeutic effect of the immune system activating drugs and improve safety and effectiveness.

11.3 Conclusion

UPy-PEG hydrogels can be used as effective formulation vehicles for the local and sustained release of TLR-agonists.

Comparative Example 1—Drug Release From a Thermoreversible (RT) Gel Platform

Comp. Ex 1.1 Materials and Methods

Hydrogel Formulation

RTGel hydrogel was formulated using the following ingredients and quantities:

| | |
|---|---|
| Pluronic F-127 | 27 wt % |
| PEG400 | 1.1 wt % |
| HMC | 0.2 wt % |
| $H_2O$ | 71.7 wt % |

Pluronic F127 (Poloxamer 407) is a triblock copolymer consisting of a central hydrophobic block of polypropylene glycol (57 units) flanked by two hydrophilic blocks of polyethylene glycol (PEG) (101 units). PEG400 is a polyethylene glycol (400 units). HMC is hydroxymethylcellulose.

Drug Release Experiments

Figure 10:
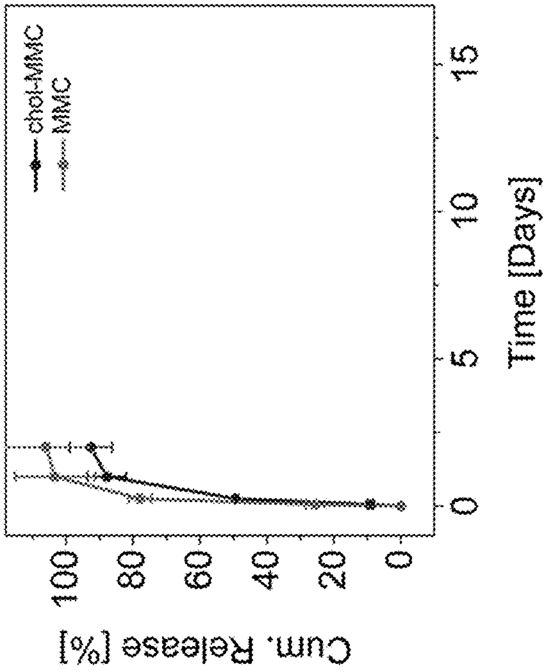
FIG. 10 shows the cumulative release of mitomycin C and chol-MMC from a thermoreversible RTGel hydrogel.

Mitomycin C and chol-MMC were loaded from a stock solution (30 mM in DMSO) to 0.4 mM in the hydrogel solution. The drug loaded solution (100 μL) was cooled and transferred to a Millicell insert, which was placed in a 24-wells plate filled with PBS pH 7.4 (600 μL). At set time points the PBS was refreshed and the removed PBS was analyzed for drug content UV absorbance at 363 nm. Release experiments were performed with n=3. The results are shown in FIG. 10.

Comp. Ex. 1.2 Results

For comparison, drug release experiments were performed with a thermoreversible hydrogel based on Pluronic F-127 polymers. These polymers comprise hydrophobic blocks and are able to retain hydrophobic drug molecules. Using the same experiment to measure the drug release, the applicant shows that a hydrophilic drug (mitomycin C) is released quickly within 1-2 days, similarly to the UPy-PEG hydrogel of the described invention (Examples 3 and 6). However, also the hydrophobic model drug compound chol-MMC is released quickly by the Pluronic-based hydrogel despite the hydrophobic compartments. During the course of the drug release experiments, the hydrogel dissolved rapidly, which is a common trait of Pluronic polymers. In contrast, the UPy-PEG hydrogel remains stable longer in identical experimental conditions and enables a more prolonged drug release of especially hydrophobic compounds such as chol-MMC (example 3).

Comp. Ex. 1.3 Conclusion

Thermoreversible hydrogels based on Pluronic-polymers are unsuitable for the long-term (days) drug release of hydrophobic drug.

Comparative Example 2—Intraperitoneal Administration of Telechelic UPy-PEG Hydrogels Comp. Ex. 2.1 Materials and Methods Hydrogelator Synthesis The tested hydrogels comprised the bifunctional telechelic UPy-PEG10k polymer. This polymer is synthesized as follows:

CDI-activation of PEG prepolymers: Solid poly(ethylene glycol) with molecular weight 10 or 20 kDa (PEG; 1 eq, usually 2-5 grams) was added to a solution of 1,1-carbonyldiimidazole (CDI; 8 eq) in dichloromethane (10-15 mL/g PEG, depending on solution viscosity and allowed to stir at room temperature for 8 hours. Excess CDI and imidazole were removed by precipitation by slowly diluting the dichloromethane solution with diethyl ether while stirring vigorously. The precipitating material was stirred for 10-20 minutes, then allowed to settle down for 10 minutes. Solid product was filtered off using vacuum filtration on a glass fritted filter followed by brief drying with nitrogen flow. Upon initial precipitation, the polymer was reprecipitated and lightly dried with nitrogen. The CDI-activated poly (ethylene glycol) was used immediately upon isolation of the solid polymer.

Diamine-termination of PEG prepolymers: CDI-activated PEG polymer (1 eq; 1-4 g) was dissolved under a N2 atmosphere in dichloromethane (15 mL/g PEG) and was added dropwise to a solution of 1,12-diaminododecane (6-8 eq) in chloroform over 30 minutes and was allowed to stir at room temperature for 8 hours. A small amount of methanol (~25 vol. %) was added to the reaction mixture to aid in the diamine solubility during precipitation and to facilitate removal. Excess 1,12-diaminododecane was then removed via precipitation from dichloromethane chloroform solutions into diethyl ether as performed in the previous step. This procedure was also performed twice. The isolated polymer was vacuum dried overnight. 1H NMR (400 MHz, CDCl3): δ=4.9 (2H, urethane), 4.2 (4H, next to urethane), 3.9-3.2 (4nH, PEG), 3.1 (4H, next to urethane), 2.7 (4H, next to amine), 2.0 (4H, broad, next to urethane), 1.5-1.1 (16H, hexyl spacer or 48H, dodecyl spacer) ppm.

UPy-functionalization with UPy-isocyanate: Solid 2(6-isocyanatohexylaminocarbonylamino)-6-methyl-4[1H]pyrimidinone (2.5 eq) was added to a solution of solid diamine terminated-PEG (1 eq; 1-2 g) in a 1:1 mixture of dichloromethane and chloroform, and was stirred at room temperature for 16 hours. Excess UPy-isocyanate was trapped via addition of silica gel (3-5 g) and dibutyltindilaurate catalyst (1 drop) to the reaction mixture and heating for 2-3 hours at reflux temperature. Upon concentration of the filtered solutions to a noticeable viscosity increase, reprecipitation was performed by dilution with diethyl ether. Polymers were vacuum dried at 40° C. for 8 hours prior to structural characterization. 1H NMR (400 MHz, CDCl3): δ=13.1 (2H, UPy), 11.8 (2H, UPy), 10.1 (2H, UPy), 5.8 (2H, UPy alkylidene), 4.9 (2H, urethane), 4.7 (2H, urea), 4.5 (2H, urea), 4.2 (4H, next to UPy), 3.8-3.3 (4nH, PEG), 3.3 (4H, next to urethane), 3.1 (12H, next to urethane and urea), 2.2 (6H, methyl at UPy), 1.6-1.1 (56H, hexyl and dodecyl spacer) ppm.

Hydrogel Formulation

The tested hydrogel formulation was the $UPy\text{-}PEG_{10k}$ 5 wt % in PBS pH 9.0.

Post Mortem Intraperitoneal Distribution of Different UPy-PEG Formulations

UPy-PEG formulations (2, 5, 7.5, and 10 wt %, total volume 5 ml) were directly administered to deceased surplus rats via an i.p. injection with an 18 G needle. During the 40 minutes after the application of the UPy-PEG hydrogel, the core temperature of the animals was kept warm (around 37 degrees Celsius) and the animals were turned around multiple times, allowing the UPy-PEG hydrogel to distribute optimally through the abdominal cavity. Then, the abdomen was reopened, and the distribution of the gel was assessed by visually inspection.

Com. Ex 2.2 Results

Hydrogel formulations based on the $UPy\text{-}PEG_{10k}$ polymer could be injected as a liquid using a needle. Inside the peritoneal cavity the solution transitions to a semisolid hydrogel. However due to its poor mechanical properties, the hydrogel disintegrates into small fragments and does not form a continuous adhesive layer on the peritoneum.

Comp. Ex. 2.3 Conclusion

The telechelic UPy-PEG10k polymer does not form a suitable hydrogel after intraperitoneal administration.

The invention claimed is:

1. A method of treating a peritoneal disease in a subject in need thereof, comprising:

administering an effective amount of a hydrogel composition to the subject, the hydrogel composition comprising a UPy-PEG polymer and a pharmaceutically acceptable carrier, wherein the UPy-PEG polymer is obtained by reacting:

a compound A with formula (I)

(I)

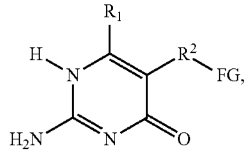

a diisocyanate compound B of formula OCN—$R^3$—NCO, and a polyethylene glycol polymer C having a number average molecular weight ($M_n$) of 250 to 50,000 Da, wherein:

$R^1$ is independently selected from the group consisting of hydrogen and $C_1$-$C_{20}$ alkyl, $R^2$ is a $C_1$-$C_{20}$ alkyl, FG is a functional group selected from OH and N($R^1$)H, and $R^3$ is a $C_2$-$C_{16}$ alkyl or a $C_4$-$C_{16}$ alkenyl.

2. The method of claim 1, wherein $R^1$ is a $C_1$-$C_5$ alkyl, $R^2$ is a $C_1$-C5 alkyl, $R^3$ is a $C_4$-$C_{10}$ alkyl, and FG is OH.

3. The method of claim 1, wherein the UPy-PEG polymer has a number average molecular weight ($M_n$) of 5,000 to 1,000,000 Da.

4. The method of claim 1, wherein compound A, diisocyanate compound B and polyethylene glycol polymer C are reacted in a molar ratio C:(A+B) of 1:1 to 1:15.

5. The method of claim 1, wherein the hydrogel composition comprises:

a viscosity of 1 to 2000 mPa·s over a temperature range of 15 to 25° C. and a pH range of 8 to 14;

a viscosity of at least 100 mPa·s over a temperature range of 35 to 40° C. and a pH range of 6 to 8; and wherein the viscosity is measured at a shear rate of 1 $s^{-1}$.

6. The method of claim 1, wherein the concentration of the UPy-PEG polymer in the pharmaceutically acceptable carrier is 0.5 to 20 wt. %, based on the total weight of the hydrogel composition.

7. The method of claim 1, wherein the pharmaceutically acceptable carrier is an aqueous solution comprising water and a buffer.

8. The method of claim 1, wherein the hydrogel composition further comprises a pharmaceutically active agent.

9. The method of claim 8, wherein the pharmaceutically active agent is selected from the group consisting of antineoplastic drugs, chemotherapeutic agents, monoclonal antibodies, immunomodulating compounds, targeted therapies and combinations thereof.

10. The method of claim 9 wherein the antineoplastic drugs and chemotherapeutic agents are selected from the group consisting of mitomycin C, oxaliplatin, carboplatin, cisplatin, gemcitabine, 5-fluorouracil, paclitaxel, docetaxel, irinotecan, doxorubicin and combinations thereof; and/or the immunomodulating compounds are selected from TLR-agonists, STING-agonists and combinations thereof; and/or the targeted therapies are selected from ATR-inhibitors, PARP-inhibitors and combinations thereof.

11. The method of claim 8, further comprising sustained release of the pharmaceutically active agent in the peritoneal cavity after administration of the hydrogel composition at a rate of more than 80% in a time of 2 to 30 hours for a hydrophilic active agent and of more than 80% in a time of 2 to 30 days for a hydrophobic active agent.

12. The method of claim 1, wherein the peritoneal disease is peritoneal carcinomatosis or peritoneal metastasis.

13. The method of claim 1, wherein the hydrogel composition is administered to a peritoneal cavity.

14. The method of claim 13, wherein the hydrogel composition is administered via catheter, via injection or using nebulization.

15. The method of claim 2, wherein $R^1$ is a methyl group.

16. The method of claim 2, wherein $R^2$ is an ethyl group.

17. The method of claim 2, wherein $R^3$ is a hexyl group.

18. The method of claim 3, wherein the UPy-PEG polymer has a number average molecular weight ($M_n$) of 15,000 to 100,000 Da.

19. The method of claim 4, wherein the molar ratio C:(A+B) is 1:2 to 1:11.

20. The method of claim 6, wherein the concentration of the UPy-PEG polymer in the pharmaceutically acceptable carrier is 1 to 10 wt. %, based on the total weight of the hydrogel composition.

* * * * *